United States Patent
Hu et al.

(10) Patent No.: US 12,291,732 B2
(45) Date of Patent: May 6, 2025

(54) METHOD OF PRODUCING A SIALYLATED N-GLYCOSYLATED RECOMBINANT PROTEIN IN PERIPLASM OF A RECOMBINANT ESCHERICHIA COLI

(71) Applicant: Dalian University, Liaoning (CN)

(72) Inventors: Xuejun Hu, Liaoning (CN); Yao Ruan, Liaoning (CN); Ning Ding, Liaoning (CN); Xin Fu, Liaoning (CN); Jing Zhu, Liaoning (CN)

(73) Assignee: Dalian University, Dalian (CN)

( * ) Notice: Subject to any disclaimer, the term of this patent is extended or adjusted under 35 U.S.C. 154(b) by 932 days.

(21) Appl. No.: 17/338,525

(22) Filed: Jun. 3, 2021

(65) Prior Publication Data

US 2021/0292801 A1 Sep. 23, 2021

Related U.S. Application Data

(63) Continuation of application No. PCT/CN2019/072202, filed on Jan. 17, 2019.

(30) Foreign Application Priority Data

Dec. 27, 2018 (CN) .......................... 201811615104.8

(51) Int. Cl.
C12P 21/00 (2006.01)
C12N 9/10 (2006.01)
C12N 15/70 (2006.01)

(52) U.S. Cl.
CPC .......... *C12P 21/005* (2013.01); *C12N 9/1048* (2013.01); *C12N 15/70* (2013.01)

(58) Field of Classification Search
CPC ............................... C12P 21/005; C12N 15/70
See application file for complete search history.

(56) References Cited

U.S. PATENT DOCUMENTS

2016/0032344 A1* 2/2016 Merritt ................. C12N 9/1051
435/254.11

FOREIGN PATENT DOCUMENTS

| CN | 101343635 A | 1/2009 |
|---|---|---|
| CN | 101415834 A | 4/2009 |
| CN | 106191087 A | 12/2016 |
| CN | 107904254 A | 4/2018 |

OTHER PUBLICATIONS

Ding et al., Feb. 8, 2017, "Increased glycosylation efficiency of recombinant proteins in Escherichia coli by auto-induction" Biochemical and Biophysical Research Communications, 485(2017), p. 138-143 and Supplemental Data (Year: 2017).*
Drouillard et al., Feb. 24, 2010, "Efficient synthesis of 60-sialyllactose, 6,60-disialyllactose, and 60-KDO-lactose by metabolically engineered E. coli expressing a multifunctional sialyltransferase from the Photobacterium sp. JT-ISH-224" Carbohydrate Research, 345(2010), p. 1394-1399 (Year: 2010).*
Bork et al., Feb. 6, 2009, "Increasing the Sialylation of Therapeutic Glycoproteins" Journal of Pharmaceutical Sciences, 98(10), p. 3499-3508 (Year: 2009).*
Datsenko and Wanner, Jun. 6, 2000, "One-step inactivation of chromosomal genes in Escherichia coli K-12 using PCR products" PNAS, 97(12), p. 6640-6645 (Year: 2000).*
Ding et al., Jul. 22, 2019, "Improving production of N-glycosylated recombinant proteins by leaky Escherichia coli" 3 Biotech, (2019), 9:302, p. 1-10 (Year: 2019).*
Fierfort and Samain, Feb. 6, 2008, "Genetic engineering of Escherichia coli for the economical production of sialylated oligosaccharides" Journal of Biotechnology, 134(2008), p. 261-265 (Year: 2008).*
Fry et al., 1998, "The lipopolysaccharide biosynthesis locus of Campylobacter jejuni 81116" Microbiology, 144, p. 2049-2061 (Year: 1998).*
Wacker et al., 2002, "N-Linked Glycosylation in Campylobacter jejuni and Its Functional Transfer into E. coli" Science, 298, p. 1790-1793 (Year: 2002).*
Campylobacter jejuni (strain 81116) inner core/lipid A genes galE, wlaX, waaC, wlaNA, wlaNB, rImA, rImB (partial) GenBank: AJ131360.1, available Jul. 26, 2016 (Year: 2016).*
Fierfort,N.rt al."Genetic engineering of Escherichia coli for the economical production of sialylated oligosaccharides" Journal of Biotechnology, vol. 134, No. (3-4), Apr. 30, 2008 (Apr. 30, 2008),ISSN:0168-1656,pp. 261-265.

* cited by examiner

*Primary Examiner* — Jennifer Dunston
*Assistant Examiner* — Jenna L Persons

(57) ABSTRACT

Disclosed herein is a method for producing a sialylated N-glycosylated recombinant protein in periplasm of a recombinant *Escherichia coli*. The sialylated N-glycosylated recombinant protein is produced in the periplasm of a recombinant *Escherichia coli* strain W3110ΔnanKETA:: Kan, and a sialylated oligosaccharide chain is Neu5Ac-α-2,6-Gal-β-1,4-GlcNAc-β-1,3-Gal-β-1,3-GlcNAc.

4 Claims, 4 Drawing Sheets

Specification includes a Sequence Listing.

METHOD OF PRODUCING A SIALYLATED N-GLYCOSYLATED RECOMBINANT PROTEIN IN PERIPLASM OF A RECOMBINANT ESCHERICHIA COLI

CROSS-REFERENCE TO RELATED APPLICATIONS

This application is a continuation of International Patent Application No. PCT/CN2019/072202, filed on Jan. 17, 2019, which claims the benefit of priority from Chinese Patent Application No. 201811615104.8, filed on Dec. 27, 2018. The content of the aforementioned applications, including any intervening amendments thereto, is incorporated herein by reference in its entirety.

REFERENCE TO AN ELECTRONIC SEQUENCE LISTING

The contents of the electronic sequence listing (SequenceListing.txt; Size: 45,098 bytes; and Date of Creation: Dec. 2, 2024) is herein incorporated by reference in its entirety.

TECHNICAL FIELD

This application relates to biotechnology and protein engineering, and more particularly to a method of producing a sialylated N-glycosylated recombinant protein in the periplasm of a recombinant *Escherichia coli*.

BACKGROUND

Currently, 70% of the approved protein drugs are N-glycosylated proteins. However, the drug proteins with small molecular weight are easily filtered out by the kidney during circulation in the human body, eliminated under the mediation of the asialoglycoprotein receptor and degraded by the protease in the peripheral blood. Sialylation is an effective way to improve the physical and chemical properties of the N-glycosylated proteins, and the sialylated N-glycosylated drug proteins have enhanced stability, prolonged half-life period and attenuated immune response. It has been reported that after being genetically engineered, the human embryonic kidney cell (HEK)293S can produce a recombinant protein modified by a sialylated oligosaccharide chain Neu5Ac-α-2,3-Gal-β-1,4-GlcNAc, which is not prone to elimination in the body and has no new immunogenicity. Nevertheless, the eukaryote system has a long culture period and a high culture cost. Although the sialylated N-glycosylated recombinant proteins can also be obtained through chemical methods in vitro, these methods are complicated and costly, and have a low yield. Producing the sialylated N-glycosylated recombinant protein in the periplasm of *Escherichia coli* can reduce the production cost and improve the sialylation efficiency, in which a glycosyltransferase expressed by a lsg glycosyltransferase gene cluster from *Haemophilus influenzae* can produce an oligosaccharide chain Gal-β-1,4-GlcNAc-β-1,3-Gal-β-1,3-GlcNAc in the periplasm of *Escherichia coli*, and then the N-glycosylation is performed on a recombinant protein in the presence of an oligosaccharyltransferase pglB from *Campylobacter jejuni*. So far, a method for modifying a recombinant protein by a terminally sialylated oligosaccharide chain Neu5Ac-Gal-β-1,4-GlcNAc-β-1,3-Gal-β-1,3-GlcNAc in periplasm of *Escherichia coli*, which can be used to produce the sialylated N-glycosylated drug proteins in the periplasm of *Escherichia coli*, has not been reported.

SUMMARY

To solve the above-mentioned problems, this disclosure provides a method for producing a sialylated N-glycosylated recombinant protein in the periplasm of a recombinant *Escherichia coli*, which has a rapid and efficient production process and large yield. This method does not require addition of sialic acid to a medium, reducing the production cost of the sialylated N-glycosylated recombinant protein and providing an effective way for developing the sialylated N-glycosylated drug proteins.

Technical solutions of this application are described as follows.

This application provides a method of producing a sialylated N-glycosylated recombinant protein in periplasm of a recombinant *Escherichia coli*, comprising:

cloning a glycosyltransferase LsgCDEF gene cluster (GenBank: M94855.1) from *Haemophilus influenzae*, an undecaprenyl-phosphate alpha-N-acetylglucosaminyltransferase WecA gene (Gene ID: 948789) from *Escherichia coli*, an oligosaccharide flippase pglK gene (Gene ID: 905421) from *Campylobacter jejuni*, an oligosaccharyltransferase pglB gene (Gene ID: 905417) from *Campylobacter jejuni*, a sialic-acid synthase NeuBCA gene cluster (GenBank: AF400048.1) from *Campylobacter jejuni*, an α-2,6-sialytransferase Δ16psp2,6ST gene (GenBank: AB293985.1) from Vibrionaceae *Photobacterium* sp. JT-ISH-224 and a gene of a protein to be modified with a sialylated oligosaccharide chain at the N terminus into an *Escherichia coli* expression vector through genetic recombination to construct an expression system of the sialylated N-glycosylated recombinant protein; and transferring the expression system of the sialylated N-glycosylated recombinant protein into an *Escherichia coli* strain suitable for production of the sialylated N-glycosylated recombinant protein followed by autoinduction culture in the absence of external sialic acid to produce the sialylated N-glycosylated recombinant protein.

In some embodiments, the sialylated oligosaccharide chain is Neu5Ac-α-2,6-Gal-β-1,4-GlcNAc-β-1,3-Gal-β-1,3-GlcNAc, and the gene of the protein to be modified carries a recognition sequence of the oligosaccharyltransferase pglB gene.

In some embodiments, the method comprises:
(1) constructing the *Escherichia coli* strain suitable for the production of the sialylated N-glycosylated recombinant protein;
(2) constructing the expression system of the sialylated N-glycosylated recombinant protein;
(3) producing a sialylated N-glycosylated recombinant protein crude product in the *Escherichia coli* strain suitable for the production of the sialylated N-glycosylated recombinant protein; and
(4) purifying the sialylated N-glycosylated recombinant protein crude product obtained in step (3) to obtain the sialylated N-glycosylated recombinant protein.

In some embodiments, the step (1) comprises:
knocking out a nanKETA gene cluster in a W3110 genome from *Escherichia coli* K-12 using a Red homologous recombination system to block an alternative pathway to synthesize a sialic acid to construct the *Escherichia coli* strain suitable for the production of the sialylated N-glycosylated recombinant protein;

wherein a genotype of the *Escherichia coli* strain suitable for the production of the sialylated N-glycosylated recombinant protein is defined as W3110ΔnanKETA::Kan.

In some embodiments, the step (2) comprises:

constructing the glycosyltransferase LsgCDEF gene cluster, the undecaprenyl-phosphate alpha-N-acetylglucosaminyltransferase WecA gene, the oligosaccharide flippase pglK gene and the oligosaccharyltransferase pglB gene onto the *Escherichia coli* expression vector to construct a vector capable of performing N-glycosylation; and cloning the sialic-acid synthase NeuBCA gene cluster, the α-2,6-sialytransferase Δ16psp2,6ST gene and the gene of the protein to be modified on the vector capable of performing N-glycosylation through gene recombination to construct the expression system of the sialylated N-glycosylated recombinant protein.

In some embodiments, the step (3) comprises:

transferring the expression system of the sialylated N-glycosylated recombinant protein obtained in step (2) to the *Escherichia coli* strain W3110ΔnanKETA::Kan obtained in step (1); and subjecting the *Escherichia coli* strain W3110ΔnanKETA::Kan to the auto-induction culture in the absence of external sialic acid to produce the sialylated N-glycosylated recombinant protein crude product.

Compared to the prior art, the beneficial effects of the present disclosure are described as follows.

This disclosure provides a method for producing a sialylated N-glycosylated recombinant protein in the periplasm of a recombinant *Escherichia coli* strain W3110ΔnanKETA::Kan, and a sialylated oligosaccharide chain is Neu5Ac-α-2,6-Gal-β-1,4-GlcNAc-β-1,3-Gal-β-1,3-GlcNAc. This method has reduced production time and cost, and improved sialylation efficiency. Moreover, it does not require an external sialic acid during the incubation. As a consequence, this disclosure provides a technical support for the preparation of a therapeutic sialylated N-glycosylated protein drug.

BRIEF DESCRIPTION OF THE DRAWINGS

where 5A: lectin ECA (Catalog Number: H-5901-1, EY Laboratories, Inc. (US)) for specifically recognizing Gal-β-1,4-GlcNAc; 5B: lectin SNA-I (Catalog Number: H-6802-1, EY Laboratories, Inc. (US)) for specifically recognizing Neu5Ac-α-2,6-Gal; 1: unglycosylated Fn3 recombinant protein; 2: unsialylated N-glycosylated Fn3 recombinant protein; and 3: sialylated N-glycosylated Fn3 recombinant protein.

DETAILED DESCRIPTION OF EMBODIMENTS

Figure 1:
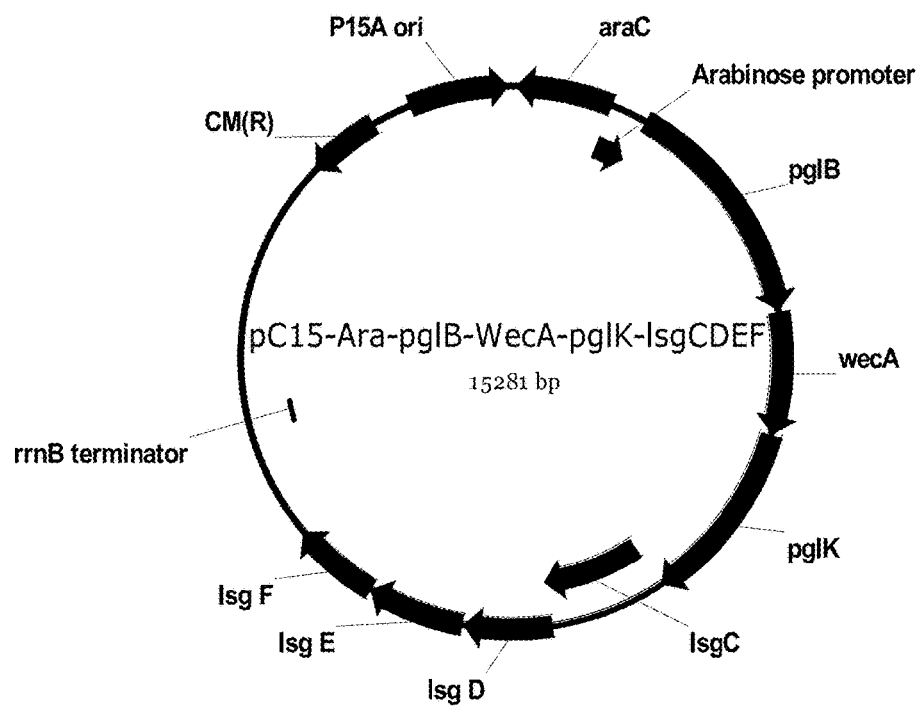
FIG. 1 schematically depicts a pC15-Ara-pglB-WecA-pglK-lsgCDEF vector.

This disclosure will be further described with reference to the accompanying drawings and the embodiments, which are not intended to limit the scope of the present disclosure. Unless otherwise specified, the experimental instruments, materials and reagents used herein are commercially available. The *Escherichia coli* strain W3110 is purchased from the Coli Genetic Stock Center of Yale University (US).

Example 1 Construction of an *Escherichia coli* Strain for Producing the Sialylated N-Glycosylated Recombinant Protein An original *Escherichia coli* strain for genetic modification was an *Escherichia coli* strain W3110 from the *Escherichia coli* line K-12. A nanKETA gene cluster (SEQ ID NO: 1) was knocked out from the genome of the strain W3110 using a Red homologous recombination system, where the involved plasmids included pKD13 and pKD46. The gene knockout of the nanKETA gene cluster was specifically described as follows.

According to the base sequences at two ends of the nanKETA gene cluster and the base sequences at two ends of a kanamycin resistance gene on the pKD13, two pairs of primers were designed for the knockout, shown as follows:

del nanKETA F1: 5'-gcatccgcgccagc-caactccccctgcgctgccgctgcgtgtaggctggagctgctt-3' (SEQ ID NO: 7);

del nanKETA R1: 5'-tggtgtacaacattccagccct-gagtgggtaaaactctgtcaaacatgagaattaa-3' (SEQ ID NO: 8);

del nanKETA F2: 5'-gtcaccctgcccggcgcgcgt-gaaaatagttttcgcatccgcgccagccaactcccct-3' (SEQ ID NO: 9);

del nanKETA R2: 5'-gcaattattgattcggcggatggtttgcc-gatggtggtgtacaacattccagccctgag-3' (SEQ ID NO: 10).

A polymerase chain reaction (PCR) amplification was conducted in the presence of the primer pair del nanKETA F1 and del nanKETA R1 using the pKD13 as a template, and the generated PCR product was used as a template to perform another PCR amplification in the presence of the primer pair del nanKETA F2 and the del nanKETA R2 to obtain a PCR fragment. The PCR fragment had 75 bp and 71 bp sequences on two ends, which were homologous to the gene sequences at two ends of the nanKETA gene cluster. Moreover, the PCR fragment also had the kanamycin resistance gene. The PCR fragment was subjected to electrophoresis and gel extraction, and then was transferred to the *Escherichia coli* strain W3110 carrying a homologous recombinase expressed by pKD46 through electroporation and integrated into the W3110 genome through the homologous recombinase expressed by pKD46 to replace the nanKETA gene cluster, so as to obtain a transformant. The transformant was spread on a LB plate containing kanamycin (15 μg/mL) and incubated at 30° C. overnight. The grown monoclonal bacterial colony was subjected to colony PCR identification using an identification primer pair JD nanKETA F: 5'-cgcactggcaatcagttgtg-3' (SEQ ID NO: 14)

and JD nanKETA R: 5'-cgtcacgccgttctactatc-3' (SEQ ID NO: 15), and the PCR amplification product was sequenced to confirm whether the nanKETA gene cluster has been successfully knocked out.

In order to remove the plasmid pKD46, a positive monoclonal colony was picked and transferred to 3 mL of a LB liquid medium containing kanamycin (15 μg/mL), and then incubated at 42° C. for 12 hours. The bacterial suspension was spread on a LB plate containing kanamycin (15 μg/mL) and incubated at 37° C. overnight. The monoclonal bacterial colony was then subjected to a resistance selection using a LB plate containing ampicillin (100 μg/mL) and a LB plate containing kanamycin (15 μg/mL). If the bacterial colony grew on the kanamycin-containing LB plate but did not grow on the ampicillin-containing LB plate, it was indicated that the plasmid pKD46 had been removed. The *Escherichia coli* strain with the deletion of the nanKETA gene cluster was named as W3110 ΔnanKETA::Kanmm, in which an alternative pathway for synthesizing sialic acid was blocked.

The LB solid medium was prepared by dissolving 10 g/L of tryptone, 5 g/L of yeast extract, 10 g/L of sodium chloride and 15 g/L of agar powder in ddH$_2$O.

The LB liquid medium was prepared by dissolving 10 g/L of tryptone, 5 g/L of yeast extract and 10 g/L of sodium chloride in ddH$_2$O.

Example 2 Construction of an Expression Vector of the Sialylated N-Glycosylated Recombinant Protein (1) Construction of N-Glycosylation Mechanism The glycosyltransferase LsgCDEF gene cluster (GenBank: M94855.1), the undecaprenyl-phosphate alpha-N-acetylglucosaminyltransferase WecA gene (Gene ID: 948789), the oligosaccharide flippase pglK gene (Gene ID: 905421) and the oligosaccharyltransferase pglB gene (Gene ID: 905417) were constructed on a vector pACYC184 using conventional gene recombination technology, and an Arabinose promoter (Ara) was introduced to regulate expressions of these genes to obtain a vector pC15-Ara-pglB-WecA-pglK-lsgCDEF (as shown in FIG. 1) for performing N-glycosylation. A sequence of the vector pC15-Ara-pglB-WecA-pglK-lsgCDEF was shown in SEQ ID NO: 2.

(2) Construction of Synthesis and Transfer Pathways of Sialic Acid

Figure 2:
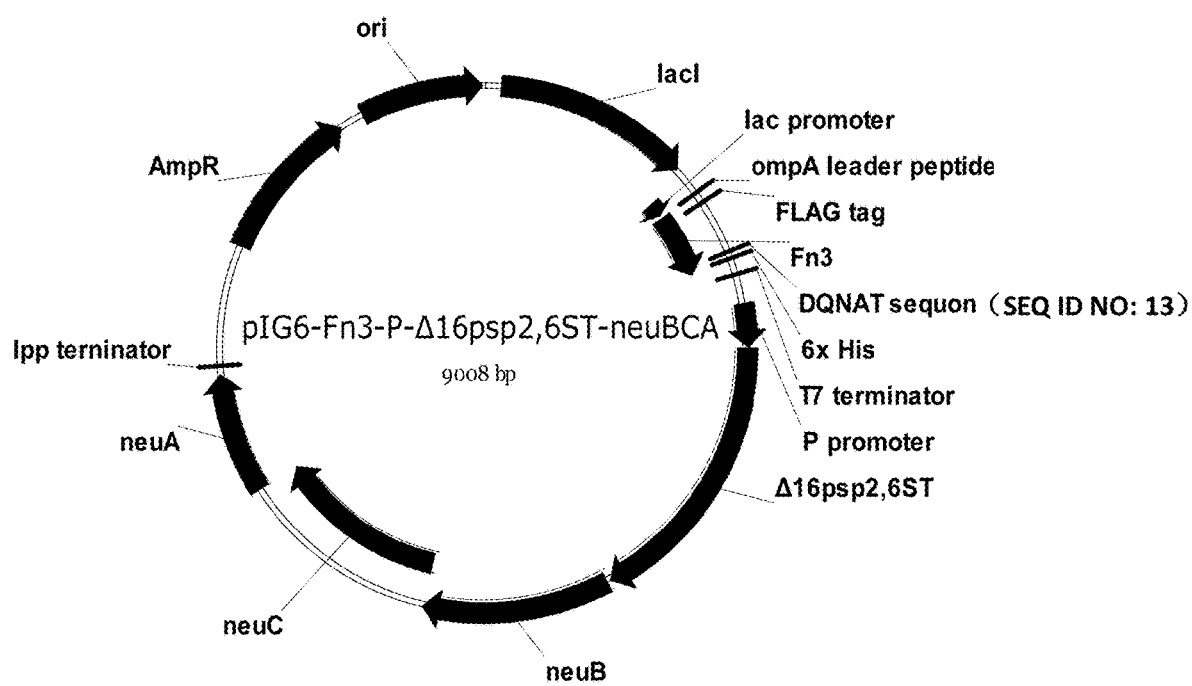
FIG. 2 schematically depicts a pIG6-Fn3-P-Δ16psp2,6ST-neuBCA vector, where a sequence of DQNAT is shown in SEQ ID NO: 13.
Figure 3:
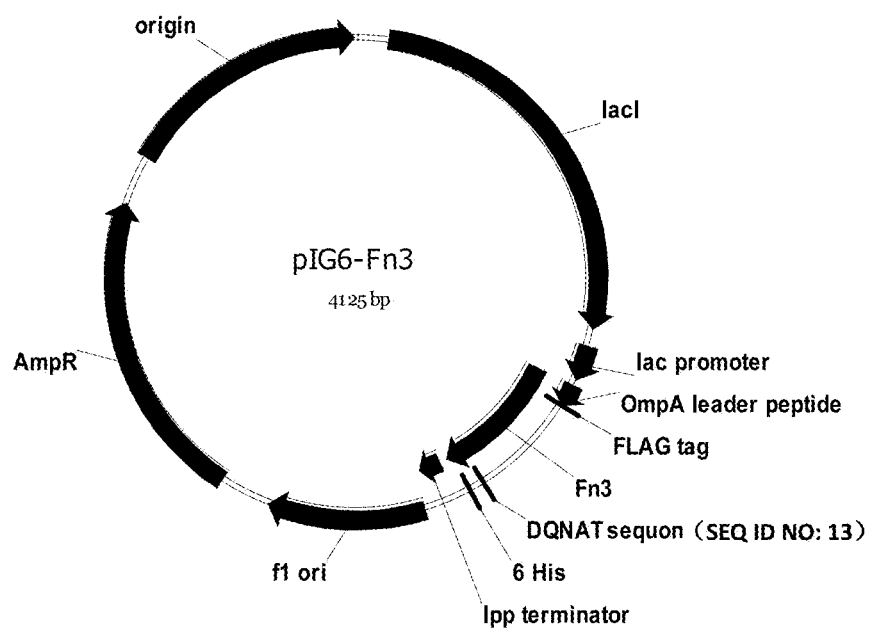
FIG. 3 schematically depicts a pIG6-Fn3vector, where the sequence of DQNAT is shown in SEQ ID NO: 13.

A recombinant human fibronectin type III domain (Fn3) was used herein as a receptor protein to instigate the sialylation of N-glycosylated recombinant protein in the periplasm of *Escherichia coli*. The gene encoding the recombinant protein Fn3 carried a FLAG tag-coding (amino acid sequence: DYKD (SEQ ID NO: 12), in which D was an aspartic acid residue; Y was a tyrosine residue; and K was a lysine residue) sequence at the 5'-end to facilitate the Western Blotting analysis, and carried a sequence encoding a recognition site DQNAT (SEQ ID NO: 13) (D was aspartic acid residue; Q was a glutamine residue; N was an asparagine residue; A was an alanine residue; and T was threonine residue) of the oligosaccharyltransferase pglB at the 3'-end. Moreover, a 6×histidine tag sequence was introduced downstream of the sequence encoding recognition site DQNAT (SEQ ID NO: 13) for the separation and purification of the recombinant protein. The gene (SEQ ID NO: 3) encoding the recombinant protein Fn3, the sialic acid synthase NeuBCA gene cluster (GenBank: AF400048.1), the α-2,6-sialytransferase Δ16psp2,6ST gene (GenBank: AB293985.1) from Vibrionaceae *Photobacterium* sp. JT-ISH-224 and a 332 bp regulatory sequence (abbreviated as P, SEQ ID NO: 4) from upstream of the Pgl gene cluster (GenBank: Y11648.1) from *Campylobacter jejuni* were cloned to a vector pIG6, so as to obtain an expression vector pIG6-Fn3-P-Δ16psp2,6ST-neuBCA (as shown in FIG. 2) of the recombinant protein Fn3 and the synthase and transferase of sialic acid. A sequence of the expression vector pIG6-Fn3-P-Δ16psp2,6ST-neuBCA was shown in SEQ ID NO: 5. Further, the gene encoding the recombinant protein Fn3 was cloned to the vector pIG6 alone to obtain a Fn3 expression vector pIG6-Fn3 as control (as shown in FIG. 3). A sequence of the expression vector pIG6-Fn3 was shown in SEQ ID NO: 6.

Example 3 Production of the Sialylated N-Glycosylated Recombinant Protein in *Escherichia coli* and Purification The vector pC15-Ara-pglB-WecA-pglK-lsgCDEF and the vector pIG6-Fn3-P-Δ16psp2,6ST-ne-uBCA were co-transferred into the recombinant *Escherichia coli* strain W3110 ΔnanKETA::Kan to obtain a recombinant *Escherichia coli* strain carrying the expression vector of the sialylated N-glycosylated recombinant protein.

The transformant was inoculated onto an LB plate containing kanamycin (15 μg/mL), ampicillin (100 μg/mL) and chloramphenicol (34 μg/mL), and incubated overnight at 37° C. for 12 hours. Then the monoclone was picked and inoculated into 3 mL of an LB liquid medium containing ampicillin (100 μg/mL) and chloramphenicol (34 μg/mL), and then incubated at 220 rpm and 37° C. overnight. On the next day, the bacterial suspension was inoculated into 500 mL of an auto-induction medium containing ampicillin (100 μg/mL) and chloramphenicol (34 μg/mL) at a ratio of 1:100 (v/v), and incubated at 220 rpm and 25° C. for 40 hours, during which L-arabinose (200 μg/mL) was added as an inducer every 12 hours. Then the bacterial suspension was centrifuged at 4000 rpm and 4° C., and the cells were collected, and then subjected to ultrasonic disruption and high-speed low-temperature centrifugation to obtain a supernatant containing a sialylated N-glycosylated Fn3 recombinant protein. A nickel column was equilibrated with 10 column volumes of an equilibration buffer. The supernatant was loaded onto the nickel column at a low speed, and then the nickel column was eluted with 20 column volumes of a 20 mM imidazole buffer and then underwent gradient elution with 40 mM, 60 mM, 120 mM, 240 mM and 500 mM imidazole buffers, respectively. The eluate was collected, and then subjected to separation and purification to obtain the sialylated N-glycosylated Fn3 recombinant protein, where the sialylated oligosaccharide chain was Neu5Ac-α-2,6-Gal-β-1,4-GlcNAc-β-1,3-Gal-β-1,3-GlcNAc. The purified sialylated N-glycosylated Fn3 recombinant protein was desalted using a desalting column and stored at 4° C. for use.

At the same time, an *Escherichia coli* strain W3110 ΔnanKETA::Kan only carrying the vector pIG6-Fn3 and an *Escherichia coli* strain W3110 ΔnanKETA::Kan carrying the vector pIG6-Fn3 and the vector pC15-Ara-pglB-WecA-pglK-lsgCDEF were also incubated as control groups, and the specific steps were described as follows.

The vector pIG6-Fn3 was transferred into the *Escherichia coli* strain W3110 ΔnanKETA::Kan. The obtained transformant was inoculated on a LB plate containing kanamycin (15 μg/mL) and ampicillin (100 μg/mL), and incubated overnight at 37° C. for 12 hours. A monoclone was selected and inoculated into 3 mL of a LB liquid medium containing ampicillin (100 μg/mL), and then incubated at 220 rpm and 37° C. overnight. On the next day, the bacterial suspension at a ratio of 1:100 was inoculated into 500 mL of an auto-induction medium containing ampicillin (100 μg/mL), and incubated at 220 rpm and 25° C. for 40 hours.

The vector pIG6-Fn3 and the vector pC15-Ara-pglB-WecA-pglK-lsgCDEF were co-transferred into the *Escherichia coli* strain W3110 ΔnanKETA::Kan. The obtained transformant was inoculated on an LB plate containing kanamycin (15 μg/mL), ampicillin (100 μg/mL) and chloramphenicol (34 μg/mL), and incubated overnight at 37° C. for 12 hours. A monoclone was selected and inoculated into 3 mL of a LB liquid medium containing ampicillin (100 μg/mL) and chloramphenicol (34 μg/mL), and then incubated at 220 rpm and 37° C. overnight. On the next day, the bacterial suspension at a volume ratio of 1:100 was inoculated into 500 mL of an auto-induction medium containing ampicillin (100 μg/mL) and chloramphenicol (34 μg/mL), and incubated at 220 rpm and 25° C. for 40 hours, during which L-arabinose (200 μg/mL) was added as an inducer every 12 hours.

The cell collection, purification and desalination were the same as those mentioned in the preparation of the sialylated N-glycosylated Fn3 recombinant protein, and an unglycosylated Fn3 recombinant protein and an unsialylated N-glycosylated Fn3 recombinant protein were obtained, respectively.

The LB solid medium was prepared by dissolving 10 g/L of tryptone, 5 g/L of yeast extract, 10 g/L of sodium chloride and 15 g/L of agar powder in ddH$_2$O.

The LB liquid medium was prepared by dissolving 10 g/L of tryptone, 5 g/L of yeast extract and 10 g/L of sodium chloride in ddH$_2$O.

The auto-induction medium was prepared by dissolving 10 g/L of tryptone, 5 g/L of yeast extract, 5 g/L of glycerol, 0.5 g/L of glucose, 2 g/L of lactose, 7.1 g/L of disodium hydrogen phosphate, 6.8 g/L of potassium dihydrogen phosphate, 3.3 g/L of ammonium sulfate, 0.9 g/L of sodium sulfate and 0.25 g/L of magnesium sulfate heptahydrate in ddH$_2$O.

Example 4 Detection of the Sialylated N-Glycosylated Recombinant Protein Produced in *Escherichia coli*

The sialylation of the recombinant protein was analyzed respectively by Western Blotting, lectin blot and mass spectrometry.

Figure 4:
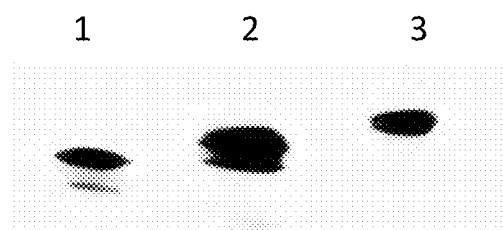
FIG. 4 shows Western Blotting results of Fn3 recombinant protein expressed in a recombinant *Escherichia coli*; where 1: unglycosylated Fn3 recombinant protein; 2: unsialylated N-glycosylated Fn3 recombinant protein; and 3: sialylated N-glycosylated Fn3 recombinant protein.

(1) In the Western Blotting analysis, an anti-FLAG M1 monoclonal antibody produced by Sigma-Aldrich LLC. (Germany) was used as a primary antibody, and a horseradish peroxidase-labeled goat anti-mouse IgG produced by Solarbio Life Sciences Co., Ltd. (Beijing, China) was used as a secondary antibody; the purified and desalted unglycosylated Fn3 recombinant protein and the unsialylated N-glycosylated Fn3 recombinant protein were used as negative controls to analyze the sialylated N-glycosylated Fn3 recombinant protein. The N-glycosylation and sialylation of the Fn3 recombinant protein were determined by comparing molecular mobilities. The results were shown in FIG. 4, from which it can be observed that the molecular weight of the Fn3 recombinant protein was increased after the N-glycosylation, and was further increased after the sialylation.

Figure 5A:
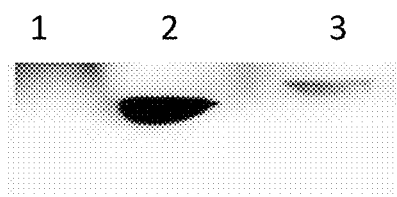
FIGS. 5A-5B show lectin blot results of the Fn3 recombinant protein expressed in the recombinant *Escherichia coli*.
Figure 5B:
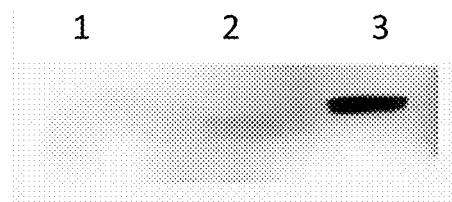

(2) With regard to the lectin blot detection, a lectin ECA (Catalog Number: H-5901-1) produced by EY Laboratories, Inc. (US) that specifically recognized Gal-β-1,4-GlcNAc and a lectin SNA-I (Catalog Number: H-6802-1) produced by EY Laboratories, Inc. (US) that specifically recognized Neu5Ac-α-2,6-Gal were used; the purified and desalted unglycosylated Fn3 recombinant protein and the unsialylated N-glycosylated Fn3 recombinant protein were used as negative controls to detect and analyze the sialylated N-glycosylated Fn3 recombinant protein. The detection result was shown in FIGS. 5A-5B. FIG. 5A illustrated the lectin blot detection results using the lectin ECA (Catalog Number: H-5901-1), in which a specific band was not detected in the purified and desalted unglycosylated Fn3 recombinant protein and the sialylated N-glycosylated Fn3 recombinant protein, whereas the specific band appeared in the unsialylated N-glycosylated Fn3 recombinant protein, proving that the Fn3 recombinant protein was N-glycosylated. FIG. 5B illustrated the lectin blot results using the lectin SNA-I (Catalog Number: H-6802-1), in which a specific band was not detected in the purified and desalted unglycosylated Fn3 recombinant protein and the unsialylated N-glycosylated Fn3 recombinant protein, whereas the specific band appeared in the sialylated N-glycosylated Fn3 recombinant protein, proving that the Fn3 recombinant protein was sialylated and N-glycosylated.

(3) Analysis of Composition of Sugar Chain of the Sialylated N-Glycosylated Fn3 Recombinant Protein The composition analysis of the sugar chain was performed as follows. The purified and desalted sialylated N-glycosylated Fn3 recombinant protein obtained in Example 3 was digested with trypsin (promega V5280) and endoproteinase Glu-C (promega), and then qualitatively detected by a Thermo Orbitrap Exactive HF liquid chromatograph-mass spectrometer (LC-MS). The main glycoform involved in the modification was determined according to b and y ions of the secondary spectrogram and the match of mass number.

Detector: Thermool Orbitrap Exactive HF mass spectrometer (Thermo Fisher).

Figure 6A:
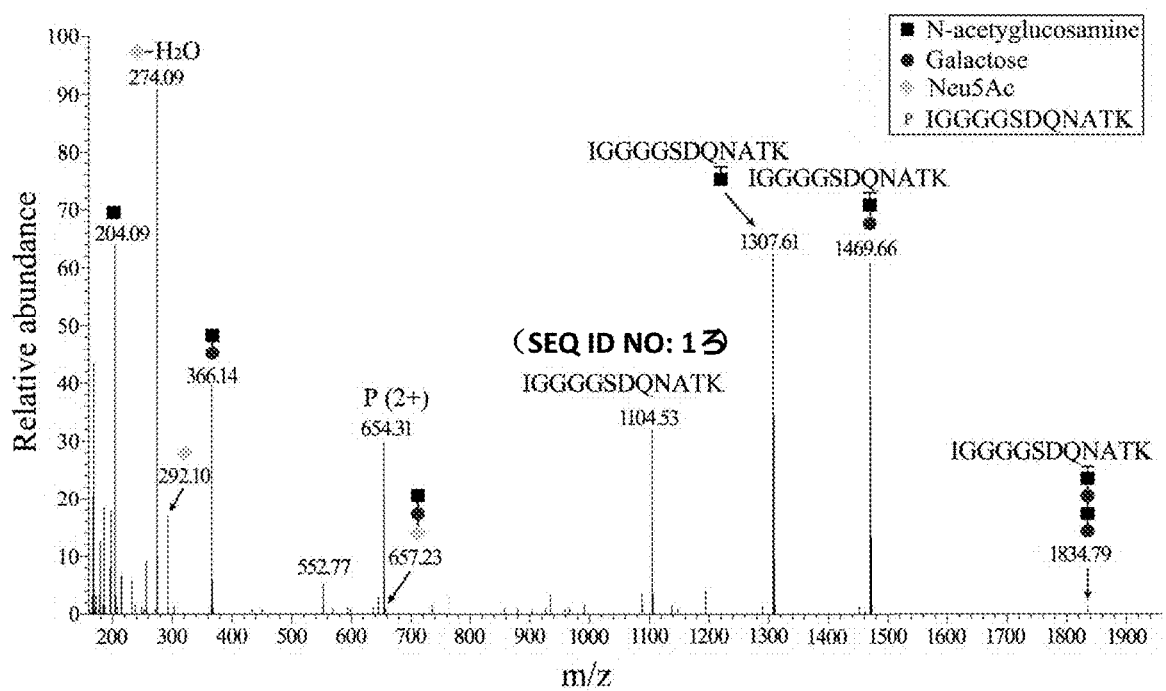
FIGS. 6A-6B show the composition of an oligosaccharide chain of the sialylated N-glycosylated recombinant protein; where 6A: high-energy collision-induced dissociation (HCD) mass spectroscopy/mass spectroscopy (MS/MS) spectrum; and 6B: deconvoluted MS/MS spectrum, where a sequence of IGGGGSDQNATK is shown in SEQ ID NO: 11.
Figure 6B:
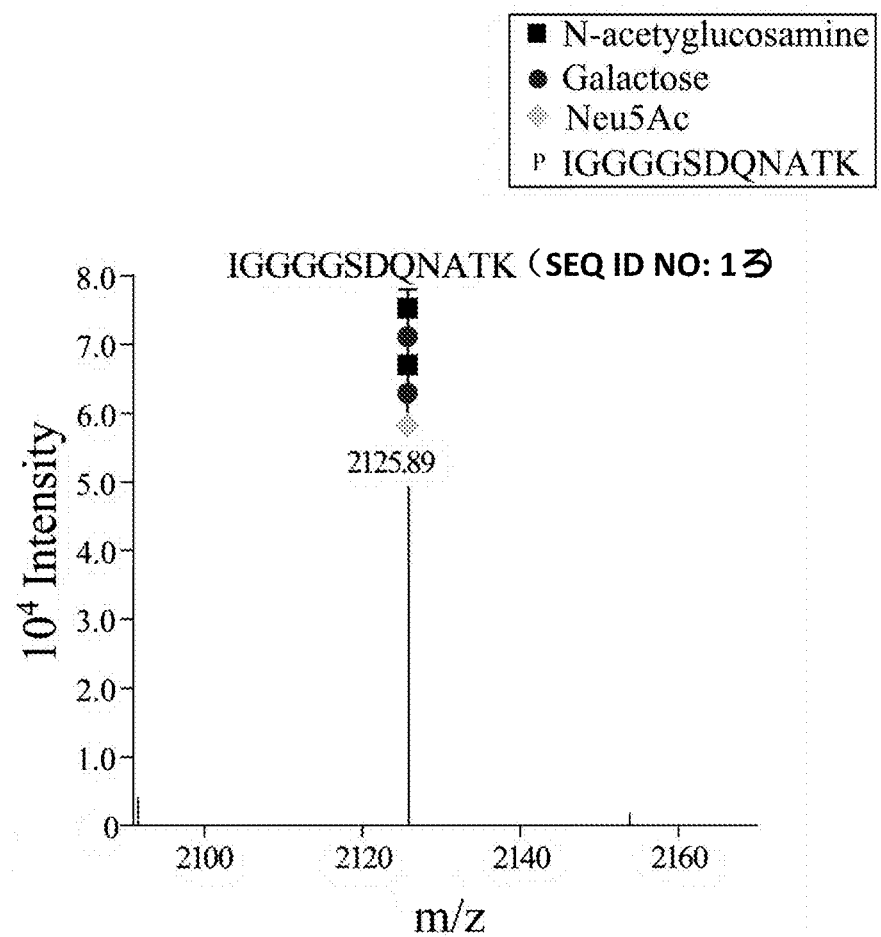

Mobile phase: A: 0.1% formic acid+99.9% water; B: 99.9% acetonitrile+0.1% formic acid; flow rate: 0.6 μL/min. The analysis result was shown in FIGS. 6A-6B. The glycopeptide was IGGGGSDQNATK with a molecular weight of 1104.1, where I: isoleucine residue; G: glycine residue; S: serine residue; D: aspartic acid residue; Q: glutamine residue; N: asparagine residue; A: alanine residue; T: threonine residue; and K: lysine residue. The modification site was located at the asparagine residue. FIG. 6A showed specific peaks of NeuAc (molecular weight: 292.10), NeuAc-H$_2$O (molecular weight: 274.09) and NeuAc(1)Hex(1)HexNAc (1) (molecular weight: 657.23). After deconvolution, a specific peak of a glycopeptide IGGGGSDQNATK (SEQ ID NO: 11) carrying a glycan NeuAc(1)Hex(2)HexNAc(2) (molecular weight: 2125.89) was found in FIG. 6B. A glycopeptide IGGGGSDQNATK (SEQ ID NO: 11) carrying glycan Hex(2)HexNAc(2) (molecular weight: 1634.79), a glycopeptide IGGGGSDQNATK (SEQ ID NO: 11) carrying glycan Hex(1)HexNAc(1) (molecular weight: 1469.66) and a glycopeptide IGGGGSDQNATK (SEQ ID NO: 11) carrying glycan HexNAc(1) (molecular weight: 1307.61) shown in FIG. 6A were obtained respectively after removing the NeuAc, Hex or HexNAc of the glycopeptide IGGGGSDQNATK (SEQ ID NO: 11) carrying glycan NeuAc(1)Hex(2)HexNAc(2). According to the results of the mass spectrometry analysis, the Western Blotting detection and the lectin blot detection, it was verified that the terminally sialylated oligosaccharide chain of the modified Fn3 recombinant protein was Neu5Ac-Gal-β-1,4-GlcNAc-β-1,3-Gal-β-1,3-GlcNAc.

The embodiments demonstrate that the method provided herein for producing a sialylated N-glycosylated recombinant protein in the periplasm of a recombinant *Escherichia coli* is simple and efficient, and the production cost is low, providing a technical support for producing a more stable therapeutic protein drug or a polysaccharide vaccine.

Described above are merely preferred embodiments, and other embodiments can be made according to the common technical knowledge and general methods in the field without departing from the spirit of this disclosure. Modifications, replacements and variations made by those skilled in the art according to the technical solutions and the spirit of this disclosure, such as using other *Escherichia coli* expression vectors, sialytransferase genes with the same function and receptor protein expression genes to produce sialylated N-glycosylated recombinant protein in the *Escherichia coli*, should fall within the scope of the present disclosure defined by the appended claims.

What is claimed is:

1. A method of producing a sialylated N-glycosylated recombinant protein in the periplasm of a recombinant *Escherichia coli*, comprising:
   (1) constructing an *Escherichia coli* strain suitable for production of the sialylated N-glycosylated recombinant protein;
   (2) constructing an expression system of the sialylated N-glycosylated recombinant protein, comprising:
      cloning a glycosyltransferase LsgCDEF gene cluster from *Haemophilus influenzae*, an undecaprenyl-phosphate alpha-N-acetylglucosaminyltransferase WecA gene from *Escherichia coli*, a oligosaccharide flippase pglK gene from *Campylobacter jejuni*, an oligosaccharyltransferase pglB gene from *Campylobacter jejuni*, a sialic-acid synthase NeuBCA gene cluster from *Campylobacter jejuni*, an α-2,6-sialytransferase Δ16psp2,6ST gene from Vibrionaceae *Photobacterium* sp. JT-ISH-224, a 332 bp regulatory sequence from upstream of the Pgl gene cluster from *Campylobacter jejuni*, and a gene of a protein to be modified with a sialylated oligosaccharide chain at the N terminal end, into an *Escherichia coli* expression vector through genetic recombination; and
   (3) transferring the expression system of the sialylated N-glycosylated recombinant protein into the *Escherichia coli* strain suitable for the production of the sialylated N-glycosylated recombinant protein; and culturing the *Escherichia coli* strain under auto-induction conditions to produce a protein crude product comprising the sialylated N-glycosylated recombinant protein;
   wherein the sialylated oligosaccharide is Neu5Ac-α-2,6-Gal-β-1,4-GlcNAc-β-1,3-Gal-β-1,3-GlcNAc; and
   the 332 bp regulatory sequence is shown in SEQ ID NO: 4.

2. The method of claim 1, wherein the method comprises:
   purifying the sialylated N-glycosylated recombinant protein from the protein crude product.

3. The method of claim 1, wherein the step (1) comprises:
   using a Red homologous recombination system to knock out a nanKETA gene cluster in the genome of an *Escherichia coli* K-12 W3110 strain, to thereby block an alternative pathway to synthesize a sialic acid;
   wherein the resulting genotype of the *Escherichia coli* strain suitable for the production of the sialylated N-glycosylated recombinant protein is defined as W3110ΔnanKETA::Kan.

4. The method of claim 3, wherein the step (3) comprises:
   transferring the expression system of the sialylated N-glycosylated recombinant protein obtained in step (2) to the *Escherichia coli* strain W3110ΔnanKETA::Kan obtained in step (1); and
   subjecting the *Escherichia coli* strain W3110ΔnanKETA::Kan to the culture under the auto-induction conditions in the absence of external sialic acid to produce the sialylated N-glycosylated recombinant protein crude product.

* * * * *

SEQUENCE LISTING

<160> NUMBER OF SEQ ID NOS: 15

<210> SEQ ID NO 1
<211> LENGTH: 3335
<212> TYPE: DNA
<213> ORGANISM: Artificial Sequence
<220> FEATURE:
<223> OTHER INFORMATION: synthetic

<400> SEQUENCE: 1

| | | | | | |
|---|---|---|---|---|---|
| aatgccgcga | ccagaagcaa | tcgcttccac | gcaacctgtg | cgtccacagc | cgcagactgg | 60 |
| gccgtgtgga | tcggcaagcg | tatgcccgat | atgccccgcc | agaccgccag | ggccggtaag | 120 |
| cagtttgcag | ccgctcacta | caccgccgcc | aacgccggtg | gaaacggtga | taaagaccat | 180 |
| atcggttata | tcgccatcca | gcgcctgaaa | ctccgcccat | gctgcggcct | gcgcgtcgtt | 240 |
| aatggcaatg | gtcggcaaat | tggtaagttg | ttccagcgtt | ttgactaacg | gaaagtgtag | 300 |
| caatccacca | agattatgcg | gattaagcgc | cagcaagctc | ccgtcacgga | ttatcccggt | 360 |
| cgaagcgatg | gcaacccgct | gcgcatgagc | ttgcaacgga | gagactaatg | cggataaggc | 420 |
| atcacgcaag | gcttctggtg | tctggctggc | tggcgtagga | agttcacgac | gatcgcggat | 480 |
| ctgcccgtca | gcgccaatca | gcgcggcggc | aagtttagta | ccgccgatat | caatcgccag | 540 |
| tgtggtcata | gcaccgcctt | tttcatcgct | gtgttgtacc | actgacaaat | gtgctcaaga | 600 |
| cgcgtgattg | cagaaccgac | cgtcaccgcc | cacgcgccgt | ggcgcatcgc | atccgccgcc | 660 |
| tgagcaggcg | tgttgtaacg | cccttcggca | atcacccgac | atccggcgtc | gctcaacgtt | 720 |
| ttcaccagcg | ccagatccgg | ctcttctggc | gtttcaggcg | tggtatagcc | agaaagcgta | 780 |
| gtgccaataa | tttcggctcc | cagcttttgg | catgccaggc | cgtcttccgg | cgttgagcag | 840 |
| tcggtcatcg | ccagtaaacc | gtgatggtga | atacgtgcca | gcagcgtttc | aacaggcacc | 900 |
| ggacgcgggc | ggtcggtgcc | gtcaatggcg | ataatgtccg | cgcccgcctg | cgccagcgca | 960 |
| tcaacatctt | caatataggc | cgtgatgcgt | accggagaat | cctccagatc | gcgtttcaca | 1020 |
| attccaataa | tcggcacgct | caccaccgca | cgcgtggctt | gcagatttgc | cacaccttca | 1080 |
| atgcgaatgg | caaccgcgcc | cgcctgttct | gccgctaatg | ccatggcggc | gacgatttcg | 1140 |
| ggtttatcga | gcgggctgtc | cggaaccggc | tggcaggaga | caatcaggcc | accgttagca | 1200 |
| gcgattttt | gatccagttg | tgcaagtaac | gacatacatc | ttcccttagc | gaaaggcccg | 1260 |
| gtacatagac | cgggcaacag | gattaacttt | tggttttgac | taaatcgttt | ttggcgctgc | 1320 |
| caaacggcac | ggcaccgctg | aatggtttac | cgtcgatagc | gtcatgagta | cgcaacgctt | 1380 |
| ccgggcgcaa | ccaacgctga | acgcgagaag | gcatatccag | cccaatcagc | aggatcacca | 1440 |
| cgaacgtcag | actgaacgag | agcgatgcca | gcgcagtacc | cagatccaga | cgttgagcga | 1500 |
| tcaacgcgcc | gatgattggg | gccagtgcac | cgcccaatgc | gccaacgttg | taggtaaagc | 1560 |
| ccaggcccgc | tgcacgctgg | tcggtatcga | ataaccgcc | aatcagtttt | ggtaagatcc | 1620 |
| cggcgatccc | ttgccaagc | atttgctgga | agaacagtaa | cagaccgagc | acccagacgt | 1680 |
| ttgcgccgcc | aatcgcaaat | accggaataa | tcagcagctg | cgaggccagc | aggctacaaa | 1740 |

| | |
|---|---|
| cgtacgcttt gcgggttccc agccagtcac cgaggaagcc acctacgcag catcccaccg | 1800 |
| ccgcgccaaa gccactaaag aacagcacat tggctacagt atgcgggtta taagccagat | 1860 |
| cggttttcag atacgttggc agcagcgcct gaatcggcca tgagtagagg aaagcaaaca | 1920 |
| acacgaccac catcagcatt acgcccgttg gccagcgttt gcctgcactc tgcaccataa | 1980 |
| agctgataaa gattgcggcg cataacagcc caagaacagc gacgatcgcg gcattttgca | 2040 |
| ggttaccggc gaagcagaac cacagcgcag tagccgccgc cagtgtcatt acgatattgg | 2100 |
| caatgcgatg ttcaccacgg tagagaatat ccaccattgt gcgtactggt gctttacctg | 2160 |
| cgtgtttctc tttccagtct tccgcttccg ggatgttttt acgcagccag agagcaaaga | 2220 |
| tgattggcaa aatgccgata agaacagcg cacgccagcc ccagaccgga accaccaggc | 2280 |
| tatagacctg agcggcaacg acggccccca cagagaagcc tgaaatcaaa aaaccactgg | 2340 |
| cttttgttacg cagatgtttt ggccagcttt caatgacata ggtggcgctg gaaccgtatt | 2400 |
| cacccgccat ccccatgccg atgaccagac gagcgataaa catggtgatg tagcctggcg | 2460 |
| caaagccgca ggccagcgtc ccggccgaga agagaacgat gctggtgacc attgccagac | 2520 |
| gacgcccgta gcggtcaccc atagcgccga gcatcaggcc gccgaaccag cgagagataa | 2580 |
| aggctgcaga gatcagactt gccgcctgca ccgtcgtcag cccgaattca ccttgtactt | 2640 |
| cggtgagtac cagggcgatt aaaacgaaat caaaaccgtc aagcagatat cccaaccagg | 2700 |
| cagcggaaaa tgcgcgccat tgtgcacggt tgagatggcg ataccacggg atattctggg | 2760 |
| ttgtagtact cattgtgagt ctcccgcggt gggcgatgcc cacacgcttt ggtatgaaaa | 2820 |
| ttgtagggta cagatgcgtt tatttcccct cacccggtag gggcgagcga ggggaaacaa | 2880 |
| ctcacccgcg ctcttgcatc aactgctggg ccagcgcctt cagttctggc agatattttt | 2940 |
| catctaccgg tccaaacggt tgcggcaca gcggcacaga aacgacatcc atataatgga | 3000 |
| ggacagtttt caggccgcgg aatacgcccg ttttgatcag taaatcaatg actttattgc | 3060 |
| attcagtttg cagtttctgc gcggtctgga tatcgccttc tttcagcgcc ttaacgatcc | 3120 |
| cctgatagcg ccagcccatg atgttgtagg tactgccgat accaccatca gcgcccgcca | 3180 |
| gcagaccaga ggcgaagatt tcgtcgtaac cgttatagag cacaagatca ggatgttcac | 3240 |
| gacggatctg ctccatctga tagagatcgc cagaggtctg tttcagcgca cctacgccag | 3300 |
| gcaatgtaac aagtgtgttg atctgatcca gggtc | 3335 |

<210> SEQ ID NO 2
<211> LENGTH: 15281
<212> TYPE: DNA
<213> ORGANISM: Artificial Sequence
<220> FEATURE:
<223> OTHER INFORMATION: synthetic

<400> SEQUENCE: 2

| | |
|---|---|
| agcttttatg acaacttgac ggctacatca ttcactttt cttcacaacc ggcacggaac | 60 |
| tcgctcgggc tggccccggt gcatttttta aatacccgcg agaaatagag ttgatcgtca | 120 |
| aaaccaacat tgcgaccgac ggtggcgata ggcatccggg tggtgctcaa aagcagcttc | 180 |
| gcctggctga tacgttggtc ctcgcgccag cttaagacgc taatccctaa ctgctggcgg | 240 |
| aaaagatgtg acagacgcga cggcgacaag caaacatgct gtgcgacgct ggcgatatca | 300 |
| aaattgctgt ctgccaggtg atcgctgatg tactgacaag cctcgcgtac ccgattatcc | 360 |
| atcggtggat ggagcgactc gttaatcgct tccatgcgcc gcagtaacaa ttgctcaagc | 420 |

```
agatttatcg ccagcagctc cgaatagcgc ccttcccctt gcccggcgtt aatgatttgc    480
ccaaacaggt cgctgaaatg cggctggtgc gcttcatccg ggcgaaagaa ccccgtattg    540
gcaaatattg acggccagtt aagccattca tgccagtagg cgcgcggacg aaagtaaacc    600
cactggtgat accattcgcg agcctccgga tgacgaccgt agtgatgaat ctctcctggc    660
gggaacagca aaatatcacc cggtcggcaa acaaattctc gtccctgatt tttcaccacc    720
ccctgaccgc gaatggtgag attgagaata aaccttttca ttcccagcgg tcggtcgata    780
aaaaaatcga gataaccgtt ggcctcaatc ggcgttaaac ccgccaccag atgggcatta    840
aacgagtatc ccggcagcag gggatcattt tgcgcttcag ccatactttt catactcccg    900
ccattcagag aagaaaccaa ttgtccatat tgcatcagac attgccgtca ctgcgtcttt    960
tactggctct tctcgctaac caaaccggta accccgctta ttaaaagcat tctgtaacaa   1020
agcgggacca aagccatgac aaaaacgcgt aacaaaagtg tctataatca cggcagaaaa   1080
gtccacattg attatttgca cggcgtcaca ctttgctatg ccatagcatt tttatccata   1140
agattagcgg atcctacctg acgcttttta tcgcaactct ctactgtttc tccatacccg   1200 tttttttgggc taacaggagg aattacatat gatgttgaaa aaagagtatt taaaaaaccc   1260
ttatttagtt ttgtttgcga tgattatatt agcttatgtt tttagtgtat tttgcaggtt   1320
ttattgggtt tggtgggcaa gtgagtttaa tgagtatttt ttcaataatc agttaatgat   1380
catttcaaat gatggctatg cttttgctga gggcgcaaga gatatgatag caggttttca   1440
tcagcctaat gatttgagtt attatggatc ttctttatcc gcgcttactt attggcttta   1500
taaaatcaca ccttttttctt ttgaaagtat cattttatat atgagtactt ttttatcttc   1560
tttggtggtg attcctacta ttttgctagc taacgaatac aaacgtcctt taatgggctt   1620
tgtagctgct cttttagcaa gtatagcaaa cagttattat aatcgcacta tgagtgggta   1680
ttatgatacg gatatgctgg taattgtttt gcctatgttt attttatttt ttatggtaag   1740
aatgatttta aaaaaagact ttttttcatt gattgccttg ccgttatta taggaattta   1800 tctttggtgg tatccttcaa gttatacttt aaatgtagct ttaattggac ttttttttaat   1860 ttatacactt attttttcata gaaaagaaaa gatttttttat atagctgtga ttttgtcttc   1920
tcttactctt tcaaatatag catggtttta tcaaagtgcc attatagtaa actttttgc    1980 tttattcgcc ttagagcaaa aacgcttaaa ttttatgatt ataggaattt taggtagtgc   2040
aactttgata tttttgattt taagtggtgg ggttgatcct atactttatc agcttaaatt   2100
ttatattttt agaagtgatg aaagtgcgaa tttaacgcag ggctttatgt attttaatgt   2160
caatcaaacc atacaagaag ttgaaaatgt agatcttagc gaatttatgc gaagaattag   2220
tggtagtgaa attgtttttt tgttttcttt gtttggtttt gtatggcttt tgagaaaaca   2280
taaaagtatg attatggctt tacctatatt ggtgcttggg tttttagcct taaaaggggg   2340
gcttagattt accatttatt ctgtacctgt aatggcctta ggatttggtt ttttattgag   2400
cgagtttaag gctataatgg ttaaaaaata tagccaatta acttcaaatg tttgtattgt   2460
ttttgcaact atttttgactt tagctccagt atttatccat atttacaact ataaagcgcc   2520
aacagttttt tctcaaaatg aagcatcatt attaaatcaa ttaaaaaata tagccaatag   2580
agaagattat gtggtaactt ggtgggatta tggttatcct gtgcgttatt atagcgatgt   2640
gaaaacttta gtagatggtg gaaagcattt aggtaaggat aatttttttcc cttcttttgc   2700 tttaagcaaa gatgaacaag ctgcagctaa tatggcaaga cttagtgtag aatatacaga   2760
aaaaagcttt tatgctccgc aaaatgatat tttaaaaaca gacattttgc aagccatgat   2820
```

```
gaaagattat aatcaaagca atgtggattt gtttctagct tcattatcaa aacctgattt    2880
taaaatcgat acgccaaaaa ctcgtgatat ttatctttat atgcccgcta gaatgtcttt    2940
gattttttct acggtggcta gttttcttt tattaattta gatacaggag ttttggataa     3000
accttttacc tttagcacag cttatccact tgatgttaaa aatggagaaa tttatcttag    3060
caacggagtg gttttaagcg atgattttag aagttttaaa ataggtgata atgtggtttc    3120
tgtaaatagt atcgtagaga ttaattctat aaacaaggt gaatacaaaa tcactccaat     3180
tgatgataag gctcagtttt atatttttta tttaaaggat agtgctattc cttacgcaca    3240
atttatttta atgataaaa ccatgtttaa tagtgcttat gtgcaaatgt ttttttaagg     3300
aaattatgat aagaatttat ttgacttggt gattaattct agagatgcta aggttttaa    3360 acttaaaatt taacccgaag gagatataca tatgaattta ctgacagtga gtactgatct   3420
catcagtatt ttttattca cgacactgtt tctgtttttt gcccgtaagg tggcaaaaaa    3480
agtcggttta gtggataaac caaacttccg caaacgtcac cagggattga tacctctcgt   3540
tggggggatt tcggtttacg cagggatttg cttcacgttc ggaattgtcg attactatat   3600
tccgcatgca tctctctatc tcgcttgtgc cggtgtgctt gttttcattg gcgcgctgga   3660
tgaccgtttt gatatcagcg taaaaatccg tgccaccata caggccgctg ttggcattgt   3720
tatgatggtg ttcggcaagc tttatctcag tagcctgggt tatatctttg ctcctggga   3780 gatggtgctc ggaccgtttg gttacttcct gacgctattt gccgtctggg cggccattaa   3840
tgcgttcaac atggttgatg gcattgatgg cttgctgggc gggttgtcct gcgtctcgtt   3900
tgcagcaatc ggtatgattt tgtggttcga cgggcaaacc agcctcgcaa tctggtgctt   3960
tgcgatgatc gccgccatcc tgccatacat catgcttaac cttggtatcc tgggtcgccg   4020
ctacaaagtc tttatgggtg atgcgggcag tacgctgatt ggttttaccg ttatctggat   4080
cctgctcgaa acgacccagg gcaaaaccca tcccatcagc ccggttaccg ctttgtggat   4140
aatcgccatt ccgctaatgg atatggtggc gattatgtac cgtcgcctgc gtaaaggcat   4200
gagcccattc tctcctgacc gtcagcatat tcaccatttg atcatgcgtg ccgggtttac   4260
ttcccgtcag gcgtttgtgc tgattaccct tgccgcagca ctgctcgctt ccattggcgt   4320
gctggcagaa tattctcatt ttgtcccgga gtgggtcatg ctggtgctct tttgctagc   4380 attcttcctc tatggatatt gcattaagcg tgcctggaaa gttgctcgct ttattaagcg   4440
cgtaaaacgc agactgcgta gaaatcgtgg tggcagcccc aatttaacca aataaatgag   4500
gatgtgatgc taaaaaaact tttttttatt ttaagcaagg aagataaaaa ttttttattt   4560
ttcttgcttg ttttttcagt atttgtttct tttatagaaa cttttgcgat ttctttggta   4620 atgccttta tcactttggc tagtgatttt tcttattttg atcgtaataa atatttaatc    4680
agcctaaaag aatatcttaa tatccctgtt tttgaaatca ttgtttattt tggagtgggg   4740
cttattgttt tttatgtatt tagagctttg ttaaatgcgt attattttca tcttttggca    4800
agattttcta aaggacgtta tcatgcgatc gcttataagg ttttttctaa attttttaaat   4860 attaattatg aaaaatttac tcaaaaaaat caatctgaaa ttttaaagtc cattacaggg   4920
gaagtttata atctaagcac tatgatttca tcattttac ttttgatgag tgaaatttt     4980 gtagtgctt tgctttatgc tttaatgctt ttgattaatt ataaaatcac tttatttta    5040 agtatttta tggtgttaaa tgcttttatt ttagtgaaaa tttaagccc tatcattaaa    5100 aaagcaggac taagacgcga agaagcgatg aaaaatttct tcgaaatttt aaatacaaat    5160
```

```
ttaaataatt ttaaatttat caagcttaaa accaaagaag atggagtatt aagtcttttt    5220
aaagcacaaa gtgaagcttt ttctaaagca aatattacca atgaaagcgt agctgcggtg    5280
cctagaattt atcttgaagg aataggcttt tgtgtgcttg tttttatcgt ggtattttg     5340 gttttgaaaa atgaaagtga tatttcaggt attttatcca cgatttctat ttttgtttta   5400
gcgctttatc gcttaatgcc aagcgcaaat cgtattatca caagttatca tgatttgctt    5460
tattatcatt cttctttgaa tattatttat caaaatttaa gacaagaaga agaaaatttg    5520
ggcgagggaa aattaagttt taatcaagag cttaaaattt gcaatcttag ctttggttat    5580
gagggaaaaa aatatttatt taaaaatctt aatttaaaca ttaaaaaagg tgaaaaaatc    5640
gcttttatag gggagagtgg ttgtggaaaa agtaccttag tagatcttat cataggactt    5700
ttaaaaccaa aagaagggca aattttaatt gataagcaag aattaaatgc aagtaatgca    5760
aaaaattatc gccaaaaaat aggctatatc ccgcaaaata tctatctttt taatgatagc    5820
atagctaaaa atatcacttt tggagatgcg gttgatgaag aaaaacttaa taaggttatc    5880
aaacaagcaa atttagagca ttttataaaa aatttacctc aaggagttca gacaaaagta    5940
ggcgatgggg ggagtaattt aagcggggga caaaaacaac gcatagctat agcaagggct    6000
ttgtatttag agcctgaaat tttagtgctt gatgaagcaa cttctgcgct tgatactcaa    6060
agtgaagcaa aaatcatgga tgaaatttat aaaatttcta agataaaaac catgattatt    6120
atcgcacatc gcctttctac gataacgcaa tgtgataagg tttatcgttt agaacacggt    6180
aagcttaaag aggagaaatg agggataacg agggcaaaaa atgaaaaaaa ttggtttctt    6240
tataatgaat atcgaaagtg cgggtggaac ggagcgcgtt tccattaatg ttgctaatgc    6300
tcttgctaaa cagggatatg atgtttcttt tattagcatt ggcggtaaca agccttttt    6360 ccaaatcgat gaaagaatta atatttacgc aatgaataaa ttgccctatt cattgaaaaa    6420
agattatttt tctatcacta aaaaattaag agaattagtt aaagaattac agctggatac    6480
cttaattgtg gttgatggtg caattatgct ttttctgct ttggcgttgg ttaatttaaa    6540
tataaaacat attttatggg agcattattc tttaattttt acgggcaatc gtctcgttcg    6600
cacgctcggt aaatatttag ctgtaacaac ttgcgataaa atagttacat tgacagaagc    6660
agaaaaaacg ctgtggcaag aaaaatttaa aacaataat ataattagta ttgctaatcc    6720
aaatacgctt ttgccaaaga ataaattagc aaaattggaa aataaaacta ttttatctgt    6780
agggcattta ttttcttata aggttttga ttatttatta aaagcctggc aagttttggc    6840
aaaaaaatat ccagattgga atttaaaaat agtaggatcg ggtgaggaag aagagaattt    6900
aaaaaatctt gctaaagcat tggatattga agattcagtt aatttatttc ctcgtactaa    6960
tgatgtttct ttttatattg aaagcagttc aatttattgt ttaccttcac aaacagaagg    7020
cttgccttta gtcgttattg aagcgatggc atttggctta cctattgttg cctttaattg    7080
ttctcctggc gtaaagcaat tagtggaaca taaagaaaat ggtttctttt gtgaaaaaaa    7140
taatattgaa gaaatggtta aaggtttaga tttattaatc aataatcctg aactttatca    7200
acaaatgtca gacaaatctc gtttaatgag tgaagattat ggcattgaga aaattattga    7260
agaatggaaa gggatttat aaggaataat tttatgttaa aaaatatttt gatctctta     7320 gataaagata ttcaacgtcg gaaattattc ttttctcaaa aaaataccga ggatttccaa    7380
attttttctg ccattaatac catgcaaaaa gattgggatg aattagcctc tatttttaat    7440
attgaacaat ttaaagcaca ttattttcgt aatgtcacta agggcgagat cggttgtacc    7500
ttaagccatc tttcggtata tcaaaaaatt gttgaagaca acgatattgc tgaagatagc    7560
```

```
tatgcgttag tctgtgaaga tgatgcttta ttccacttag attttcagca aaatttaacc    7620 gcactttat  cagaaaaact tgaggctgaa attatattgc ttggacagtc aaacattaat    7680
aatttcaatg atactgattt agaaattaat tatccgacaa cttttcttt  tctatgcaaa    7740 aaaacaggca atgtaaatta cgctttccct tataaaagtt attttgctgg cacggtgggt    7800
tatcttataa aaaatcagc  ggcaagaaga tttatccagc aaatttccca aaataaacca    7860
ttttggttag cggatgattt tttactcttt gaacagaatt ttaatataag aaataaagtg    7920
gttcgccctc tcatggtaat tgaaaatcct gtattgataa gcaatttaga aagtgttcgt    7980
ggatctttat ccaataattt acttaaaaaa ttaatgaaat atccattgaa aaaaatcttt    8040
gcgattaaga aaaatttggc taattaaagg aaggaattat gttaagcatt attgtgcctt    8100
cttataatcg aaaagcagaa gtgccagctt tattagaaag tttaactcaa caaacatcga    8160
gtaattttga agtgattatt gtggatgatt actccaaaga gagagtagtc gttgagcaac    8220
gctattcttt tccagttaca gtgattcgta acgaaaccaa tcaaggtgca gcggaaagtc    8280
gcaatattgg tgcgcgtgca tcaaagggcg attggttgct ttttctcgat gatgatgatc    8340 gtttatgcc  agaaaaatgt gaaaaaatac tacaagtgat tgagcaaaat ccagacatta    8400
attttattta tcatccagct aaatgtgaaa tggtcaatga agggtttact tatgtgactc    8460
aaccgattga acctcaagaa atctcgacag aacgtattt  gttagccaat aagattggtg    8520
gcatgccaat ggttgcgatt aaaaaagaga tgttttaaa  aataggtgga ttatccaccg    8580
cacttcgttc tttggaagac tatgatttct tgttaaaact gttacaagag tcaagtttta    8640
ccccttataa aattaatgaa ccactaactt attgtacttt ccatactaaa cgctcaagtg    8700
tgtctacgga taccactaat acgcaaaaag ccattgatta tattcgcgag cattatgtga    8760
aaacggtaga gcaagctcgt aattttgata ttaacgcgag ctatattttg gcttatcccc    8820
atattatgaa tttatcgcgt aaagcggcaa aatattattt tgatattttt aagaaaacaa    8880
aaagcattaa gcaatttatt attactttgg ttattttaat ttcgccaaaa ttagccatta    8940
atttaaaacg gttgggaaaa taaaatgaaa ttttcagtcc taatgtcctt atatattaag    9000
gaaaatcctc aattcttgcg ggagtgtttt gaaagtcttg gtgcacaaac tcgtcaagca    9060
gatgaaattg tcttggtttt tgatggcgta gtaacgccag aattagaatc tgttgtgaca    9120
gaatttgaaa caaaactgcc attaaaatta gttaaattgc cacaaaatcg aggattaggc    9180
aaagccttaa cgagggttt  attgcattgt gattatgact gggttttccg tatggatacg    9240
gatgatattt gcgtgcctga tcgttttgaa aagcaagtag cgtttattga acagcaccct    9300
gaaagcatca tttttggcgg acaaattgct gaatttggta aaaatgtaaa tgatattgtg    9360
gcatatcgta atgtgccaac gtcggctcaa gaaattatta aattcacgca aaacgttgt    9420 ccgtttaatc acatgacggt ggcatatcaa aaaagtgcgg tcattaattg tggtggatat    9480
gaagatcttc aagaagatta ttatttgtgg atcaaacttg tcgcacaagg tttatatatg    9540
gcgaatttgc cagatatttt agtttatgcg agagtgggaa atggtatggt gagtcgccgt    9600
cgtggcgtca atcaagctaa agcagaatgg cgtttgttca aattgaaata ccgtttggga    9660
attcagggtt tgttatctgg attatttact tttgcattgc gttttggttc tcgtttattg    9720
ccaacctcgt tattgaaaaa actttatcaa acttttttac gtaaatagga aatacgatga    9780
aattaaatat tttatttaaa attttgtttg atttgaggtt attttagttc agaaaacaat    9840
aaatataagt attgaattta cgtattatat atttgaatta ccccagcgtc gctaaaataa    9900
```

```
tttgctcttg atcaatgtga atccaaacct gttgcccgat ttgccattga tttggctggt    9960
ggactgtggc acaaaattca atgttgcttt cagcaaattg aaggatggct tcctcttcat   10020
tgagtgattt gatatttacg gggaactgat tagattgatt ctccagtggt tgttcactga   10080
tttttaccca aggagccttg aacatcagca tcacttcttt ttccgtaatg agtttcaaac   10140
gagccgagct ttttgtggta atagaaactt gcaacggcgt tggtaatcct tgcacattca   10200
catccacaac acaacgagag tcaatgattc gttgttgtgc cactcgccca aaaaattgat   10260
tgcgtgcgct actttgtaaa gaaaaacgtg cggttgccgt gagtaaacta tctaacggca   10320
cggattcatc ttgtaggata tgaaaagcgt gttcttgcgt acgttctaat aaatcataaa   10380
gctggagcaa acgctcggca taagtggtaa gcaccgtacc tccgccattt tttccacctg   10440
tatttcgttc cagcaatggg cgagggctga ttttattcat ggcttctaaa tgatcccacg   10500
cacttttata gctcactttt gcattttteg ctgcttgatt aatcgaaccg cattgttgaa   10560
tttcttgag taaacgaact cgttttggat cgataaaaag tgcttgttga agtttaattg   10620
tgagtaaaat ttcggtgttt ttcattttgc tgtccctaag taatcctaag tggtaagcct   10680
aagcgttata tattttacta ataatttttt cttttgctat atgattgtta tttatttcaa   10740
tatataatca agtaaataac gtttaatcgt aggagatgat tcctcgagat ctgcaggctg   10800
ttttggcgga tgagagaaga ttttcagcct gatacagatt aaatcagaac gcagaagcgg   10860
tctgataaaa cagaatttgc ctggcggcag tagcgcggtg gtcccacctg accccatgcc   10920
gaactcagaa gtgaaacgcc gtagcgccga tggtagtgtg gggtctcccc atgcgagagt   10980
agggaactgc caggcatcaa ataaaacgaa aggctcagtc gaaagactgg gccttaagct   11040
ttaatgcggt agtttatcac agttaaattg ctaacgcagt caggcaccgt gtatgaaatc   11100
taacaatgcg ctcatcgtca tcctcggcac cgtcaccctg gatgctgtag cataggctt    11160
ggttatgccg gtactgccgg gcctcttgcg ggatatcgtc cattccgaca gcatcgccag   11220
tcactatggc gtgctgctag cgctatatgc gttgatgcaa tttctatgcg cacccgttct   11280
cggagcactg tccgaccgct ttggccgccg cccagtcctg ctcgcttcgc tacttggagc   11340
cactatcgac tacgcgatca tggcgaccac accgtcctg tggatcctct acgccggacg   11400
catcgtggcc ggcatcaccg cgccacagg tgcggttgct ggcgcctata tcgccgacat   11460
caccgatggg gaagatcggg ctcgccactt cgggctcatg agcgcttgtt tcggcgtggg   11520
tatggtggca ggccccgtgg ccgggggact gttgggcgcc atctccttgc atgcaccatt   11580
ccttgcggcg gcggtgctca acggcctcaa cctactactg ggctgcttcc taatgcagga   11640
gtcgcataag ggagagcgtc gaccgatgcc cttgagagcc ttcaacccag tcagctcctt   11700
ccggtgggcg cggggcatga ctatcgtcgc cgcacttatg actgtcttct ttatcatgca   11760
actcgtagga caggtgccgg cagcgctctg gtcatttttc ggcgaggacc gctttcgctg   11820
gagcgcgacg atgatcggcc tgtcgcttgc ggtattcgga atcttgcacg ccctcgctca   11880
agccttcgtc actggtcccg ccaccaaacg tttcggcgag aagcaggcca ttatcgccgg   11940
catggcggcc gacgcgctgg gctacgtctt gctggcgttc gcgacgcgag gctggatggc   12000
cttccccatt atgattcttc tcgcttccgg cggcatcggg atgcccgcgt tgcaggccat   12060
gctgtccagg caggtagatg acgaccatca gggacagctt caaggatcgc tcgcggctct   12120
taccagccta acttcgatca ctggaccgct gatcgtcacg gcgatttatg ccgcctcggc   12180
gagcacatgg aacgggttgg catggattgt aggcgccgcc ctataccttg tctgcctccc   12240
cgcgttgcgt cgcggtgcat ggagccgggc cacctcgacc tgaatggaag ccggcggcac   12300
```

```
ctcgctaacg gattcaccac tccaagaatt ggagccaatc aattcttgcg gagaactgtg    12360
aatgcgcaaa ccaacccttg gcagaacata tccatcgcgt ccgccatctc cagcagccgc    12420
acgcggcgca tctcgggcag cgttgggtcc tggccacggg tgcgcatgat cgtgctcctg    12480
tcgttgagga cccggctagg ctggcggggt tgccttactg gttagcagaa tgaatcaccg    12540
atacgcgagc gaacgtgaag cgactgctgc tgcaaaacgt ctgcgacctg agcaacaaca    12600
tgaatggtct tcggtttccg tgtttcgtaa agtctggaaa cgcggaagtc ccctacgtgc    12660
tgctgaagtt gcccgcaaca gagagtggaa ccaaccggtg ataccacgat actatgactg    12720
agagtcaacg ccatgagcgg cctcatttct tattctgagt tacaacagtc cgcaccgctg    12780
tccggtagct ccttccggtg ggcgcgggc atgactatcg tcgccgcact tatgactgtc    12840
ttctttatca tgcaactcgt aggacaggtg ccggcagcgc ccaacagtcc cccggccacg    12900
gggcctgcca ccatacccac gccgaaacaa gcgccctgca ccattatgtt ccggatctgc    12960
atcgcaggat gctgctggct accctgtgga acacctacat ctgtattaac gaagcgctaa    13020 ccgttttat caggctctgg gaggcagaat aaatgatcat atcgtcaatt attacctcca    13080
cggggagagc ctgagcaaac tggcctcagg catttgagaa gcacacggtc acactgcttc    13140
cggtagtcaa taaaccggta aaccagcaat agacataagc ggctatttaa cgaccctgcc    13200
ctgaaccgac gaccgggtcg aatttgcttt cgaatttctg ccattcatcc gcttattatc    13260
acttattcag gcgtagcacc aggcgtttaa gggcaccaat aactgcctta aaaaaattac    13320
gccccgccct gccactcatc gcagtactgt tgtaattcat taagcattct gccgacatgg    13380
aagccatcac agacggcatg atgaacctga atcgccagcg gcatcagcac cttgtcgcct    13440
tgcgtataat atttgcccat ggtgaaaacg ggggcgaaga agttgtccat attggccacg    13500
tttaaatcaa aactggtgaa actcacccag ggattggctg agacgaaaaa catattctca    13560 ataaacccctt tagggaaata ggccaggttt tcaccgtaac acgccacatc ttgcgaatat    13620
atgtgtagaa actgccggaa atcgtcgtgg tattcactcc agagcgatga aaacgtttca    13680
gtttgctcat ggaaaacggt gtaacaaggg tgaacactat cccatatcac cagctcaccg    13740
tctttcattg ccatacggaa ttccggatga gcattcatca ggcgggcaag aatgtgaata    13800
aaggccggat aaaacttgtg cttattttc tttacggtct ttaaaaaggc cgtaatatcc    13860
agctgaacgg tctggttata ggtacattga gcaactgact gaaatgcctc aaaatgttct    13920
ttacgatgcc attgggatat atcaacggtg gtatatccag tgattttttt ctccatttta    13980
gcttccttag ctcctgaaaa tctcgataac tcaaaaaata cgcccggtag tgatcttatt    14040
tcattatggt gaaagttgga acctcttacg tgccgatcaa cgtctcattt tcgccaaaag    14100
ttggcccagg gcttcccgggt atcaacaggg acaccaggat ttatttattc tgcgaagtga    14160
tcttccgtca caggtattta ttcggcgcaa agtgcgtcgg gtgatgctgc caacttactg    14220
atttagtgta tgatggtgtt tttgaggtgc tccagtggct tctgtttcta tcagctgtcc    14280
ctcctgttca gctactgacg gggtggtgcg taacggcaaa agcaccgccg gacatcagcg    14340
ctagcggagt gtatactggc ttactatgtt ggcactgatg agggtgtcag tgaagtgctt    14400
catgtggcag gagaaaaaag gctgcaccgg tgcgtcagca gaatatgtga tacaggatat    14460
attccgcttc ctcgctcact gactcgctac gctcggtcgt tcgactgcgg cgagcggaaa    14520
tggcttacga acgggcgga gatttcctgg aagatgccag gaagatactt aacagggaag    14580
tgagagggcc gcggcaaagc cgttttttcca taggctccgc cccctgaca agcatcacga    14640
```

| | |
|---|---:|
| aatctgacgc tcaaatcagt ggtggcgaaa cccgacagga ctataaagat accaggcgtt | 14700 |
| tcccccctggc ggctccctcg tgcgctctcc tgttcctgcc tttcggttta ccggtgtcat | 14760 |
| tccgctgtta tggccgcgtt tgtctcattc cacgcctgac actcagttcc gggtaggcag | 14820 |
| ttcgctccaa gctggactgt atgcacgaac ccccgttca gtccgaccgc tgcgccttat | 14880 |
| ccggtaacta tcgtcttgag tccaacccgg aaagacatgc aaaagcacca ctggcagcag | 14940 |
| ccactggtaa ttgatttaga ggagttagtc ttgaagtcat gcgccggtta aggctaaact | 15000 |
| gaaaggacaa gttttggtga ctgcgctcct ccaagccagt tacctcggtt caaagagttg | 15060 |
| gtagctcaga gaaccttcga aaaaccgccc tgcaaggcgg ttttttcgtt ttcagagcaa | 15120 |
| gagattacgc gcagaccaaa acgatctcaa gaagatcatc ttattaatca gataaaatat | 15180 |
| ttctagattt cagtgcaatt tatctcttca aatgtagcac ctgaagtcag ccccatacga | 15240 |
| tataagttgt aattctcatg tttgacagct tatcatcgat a | 15281 |

<210> SEQ ID NO 3
<211> LENGTH: 429
<212> TYPE: DNA
<213> ORGANISM: Artificial Sequence
<220> FEATURE:
<223> OTHER INFORMATION: synthetic

<400> SEQUENCE: 3

| | |
|---|---:|
| atgaaaaaga cagctatcgc gattgcagtg gcactggctg gtttcgctac cgtagcgcag | 60 |
| gccgactaca agatatccg tgacctggaa gtggtcgctg ccacaccgac gagtctgctg | 120 |
| atttcttggg atgcaccagc tgtaaccgtg cgctactacc gcattactta cggggagacg | 180 |
| ggcggcaatt ccccggtgca agaatttact gttccgggca gcaaaagtac agcaactatt | 240 |
| agcggcctga aacgggcgt tgattatacc attactgttt acgcagtaac tgggcgtggc | 300 |
| gattcaccgg cgtcctctaa acctatttcg atcaactatc gtactgaaat cggtggtggt | 360 |
| ggttctgacc aaaacgcgac caagcttggt ggtggtggtt cacttgagca ccaccaccac | 420 |
| caccactga | 429 |

<210> SEQ ID NO 4
<211> LENGTH: 332
<212> TYPE: DNA
<213> ORGANISM: Artificial Sequence
<220> FEATURE:
<223> OTHER INFORMATION: synthetic

<400> SEQUENCE: 4

| | |
|---|---:|
| gggtttacca ggaaaatatg atgtgcatgg cgatgaggtg atgaaacttt tttgtgaaaa | 60 |
| tgaacttgaa aaaattcacg aatattgtga aagtgatgtt ttaaatactt atatgctttt | 120 |
| tttaaaatat gaacttatta aagctaatgt tagtgaagaa gattatattg attttctttc | 180 |
| ttatatgaga gattttttgc gtgcaaaaaa atcagatcgt tcctatacag aagttttgc | 240 |
| aaaagcttgt gagagtgaaa tttcaaaagt tcaatcttaa gtatttaaga aaatatatta | 300 |
| aaatttattt ttgatatttt ttagaaaaag ga | 332 |

<210> SEQ ID NO 5
<211> LENGTH: 9008
<212> TYPE: DNA
<213> ORGANISM: Artificial Sequence
<220> FEATURE:
<223> OTHER INFORMATION: synthetic

<400> SEQUENCE: 5

```
acccgacacc atcgaatggc gcaaaacctt tcgcggtatg gcatgatagc gcccggaaga      60
gagtcaattc agggtggtga atgtgaaacc agtaacgtta tacgatgtcg cagagtatgc     120
cggtgtctct tatcagaccg tttcccgcgt ggtgaaccag gccagccacg tttctgcgaa     180
aacgcgggaa aaagtggaag cggcgatggc ggagctgaat tacattccca accgcgtggc     240
acaacaactg gcgggcaaac agtcgttgct gattggcgtt gccacctcca gtctggccct     300
gcacgcgccg tcgcaaattg tcgcggcgat taaatctcgc gccgatcaac tgggtgccag     360
cgtggtggtg tcgatggtag aacgaagcgg cgtcgaagcc tgtaaagcgg cggtgcacaa     420
tcttctcgcg caacgcgtca gtgggctgat cattaactat ccgctggatg accaggatgc     480
cattgctgtg aagctgcct  gcactaatgt tccggcgtta tttcttgatg tctctgacca     540
gacacccatc aacagtatta ttttctccca tgaagacggt acgcgactgg gcgtggagca     600
tctggtcgca ttgggtcacc agcaaatcgc gctgttagcg ggcccattaa gttctgtctc     660
ggcgcgtctg cgtctggctg gctggcataa atatctcact cgcaatcaaa ttcagccgat     720
agcggaacgg gaaggcgact ggagtgccat gtccggtttt caacaaacca tgcaaatgct     780
gaatgagggc atcgttccca ctgcgatgct ggttgccaac gatcagatgg cgctgggcgc     840
aatgcgcgcc attaccgagt ccgggctgcg cgttggtgcg gacatctcgg tagtgggata     900
cgacgatacc gaagacagct catgttatat cccgccgtta accaccatca acaggatt t    960 tcgcctgctg gggcaaacca gcgtggaccg cttgctgcaa ctctctcagg gccaggcggt    1020
gaagggcaat cagctgttgc ccgtctcact ggtgaaaaga aaaccacccc tggcgcccaa    1080
tacgcaaacc gcctctcccc gcgcgttggc cgattcatta atgcagctgg cacgacaggt    1140
ttcccgactg gaaagcgggc agtgagcgca acgcaattaa tgtgagttag ctcactcatt    1200
aggcacccca ggctttacac tttatgcttc cggctcgtat gttgtgtgga attgtgagcg    1260
gataacaatt tcacacagga aacagctatg accatgatta cgaatttcta gataacgagg    1320
gcaaaaaatg aaaaagacag ctatcgcgat tgcagtggca ctggctggtt tcgctaccgt    1380
agcgcaggcc gactacaaag atatccgtga cctggaagtg gtcgctgcca caccgacgag    1440
tctgctgatt tcttgggatg caccagctgt aaccgtgcgc tactaccgca ttacttacgg    1500
ggagacgggc ggcaattccc cggtgcaaga atttactgtt ccgggcagca aaagtacagc    1560
aactattagc ggcctgaaac cgggcgttga ttataccatt actgtttacg cagtaactgg    1620
gcgtggcgat tcaccggcgt cctctaaacc tatttcgatc aactatcgta ctgaaatcgg    1680
tggtggtggt tctgaccaaa acgcgaccaa gcttggtggt ggtggttcac ttgagcacca    1740
ccaccaccac cactgagaat tcgagatccg gctgctaaca aagcccgaaa ggaagctgag    1800
ttggctgctg ccaccgctga gcaataacta gcataacccc ttggggcctc taaacgggtc    1860
ttgaggggtt ttttgctgaa aggaggaact atatccggat gggttaccag gaaaatatg     1920 atgtgcatgg cgatgaggtg atgaaacttt tttgtgaaaa tgaacttgaa aaattcacg     1980 aatattgtga aagtgatgtt ttaaatactt atatgctttt tttaaaatat gaacttatta    2040
aagctaatgt tagtgaagaa gattatattg attttctttc ttatatgaga gattttttgc    2100
gtgcaaaaaa atcagatcgt tcctatacag aagttttttgc aaaagcttgt gagagtgaaa   2160
tttcaaaagt tcaatcttaa gtatttaaga aaatatatta aaatttatttt tgatattttt   2220 ttagaaaaag gacatatgaa gaacttcctg ctgctgaccc tgatcctgct gaccgcgtgc    2280
aacaacagcg aggaaaacac ccagagcatc atcaagaacg atatcaacaa gaccatcatc    2340
```

```
gacgaggaat acgtgaacct ggaaccgatc aaccaaagca acattagctt taccaaacac    2400
agctgggttc agacctgcgg cacccagcaa ctgctgaccg aacaaaacaa ggagagcatc    2460
agcctgagcg tggttgcgcc gcgtctggac gatgacgaaa aatactgctt cgactttaac    2520
ggcgtgagca acaagggcga gaaatatatt accaaggtta ccctgaacgt ggttgcgccg    2580
agcctggaag tgtacgttga tcacgcgagc ctgccgaccc tgcagcaact gatggacatc    2640
attaagagcg aggaagagaa cccgaccgcg cagcgttata tcgcgtgggg tcgtattgtg    2700
ccgaccgatg aacaaatgaa agagctgaac atcaccagct tcgcgctgat taacaaccac    2760 accccgcgg acctggtgca ggagatcgtt aagcaggcgc aaaccaaaca ccgtctgaac    2820
gtgaagctga gcagcaacac cgcgcacagc ttcgataacc tggttccgat cctgaaagaa    2880
ctgaacagct ttaacaacgt gaccgttacc aacattgacc tgtacgatga cggcagcgcg    2940
gagtacgtta acctgtataa ctggcgtgat accctgaaca agaccgacaa cctgaagatc    3000
ggtaaagatt acctggaaga cgtgatcaac ggcattaacg aggataccag caacaccggt    3060
accagcagcg tttataactg gcagaagctg taccccggcga actatcactt tctgcgtaaa    3120
gactacctga ccctggaacc gagcctgcac gagctgcgtg attatatcgg cgacagcctg    3180
aagcagatgc aatgggatgg tttcaagaaa tttaacagca acagcaaga actgttcctg    3240 agcattgtga ctttgacaa gcagaaactg caaaacgagt ataacagcag caacctgccg    3300
aacttcgtgt ttaccggcac caccgttttgg gcgggtaacc acgagcgtga gtactatgcg    3360
aaacagcaaa tcaacgttat taacaacgcg atcaacgaaa gcagcccgca ctacctgggc    3420
aacagctacg acctgttctt caagggtcac ccgggtggcg gtatcattaa caccctgatt    3480
atgcagaact acccgagcat ggtggacatc ccgagcaaaa ttagcttcga agttctgatg    3540
atgaccgata tgctgccgga cgcggtggcg ggtatcgcga gcagcctgta ttttaccatt    3600
ccggcggaga agatcaaatt cattgttttt accagcaccg aaaccatcac cgatcgtgag    3660
accgcgctgc gtagcccgct ggtgcaagtt atgatcaagc tgggcattgt gaaagaagag    3720
aacgttctgt tctgggcgga cctgccgaac tgcgagaccg tgtgtgcat cgcggtttaa    3780 ataacgaggg caaaaatga aagaaataaa aatacaaaat ataatcataa gtgaagaaaa    3840 agcacccta gtcgtacctg aaataggcat taatcataat ggcagtttag aactagctaa    3900
aattatggta gatgcagcct ttagcgcagg tgctaagatt ataaagcatc aaactctatat    3960 tgttgaagat gagatgagta aggccgctaa aaagtaatt cctggtaatg caaaaataag    4020
catttatgag attatgcaaa aatgtgctt ggattataaa gatgagctag cacttaaaga    4080
atacacagaa aaattaggtc ttgttatct tagcacacct tttctcgtg caggtgcgaa    4140 ccgcttagaa gatatgggag ttagtgctt taagattggt tcaggtgagt gtaataatta    4200
tccgcttatt aaacacatag cagcctttaa aaagcctatg atagttagca caggaatgaa    4260
tagtattgaa agtataaac caactgtaaa aatcttatta gacaatgaaa ttcctttgt    4320 tttaatgcac acgaccaatc tttacccaac ccgcataat cttgtaagat taaacgctat    4380
gcttgagtta aaaaagaat tttcttgtat ggtaggctta agcgaccaca caacagataa    4440
tcttgcgtgt ttaggtgcag ttgtacttgg agcttgtgtg cttgaaagac attttactga    4500
tagtatgcat agaagtggcc ctgatatagt ttgttctatg gatacaaagg ctttaaaaga    4560
gctaattata caaagtgagc aaatggctat aataagagga aataatgaaa gtaaaaaagc    4620
ggctaaacaa gaacaagtta caattgattt tgccttgca agtgtagtta gcattaaaga    4680
tattaaaaaa ggcgaagttt tatctatgga taatatttgg gttaaaagac ctggacttgg    4740
```

```
tggaattagt gcggctgaat ttgaaaatat tttaggcaaa aaagcattaa gagatataga    4800
aaatgatgct cagttaagct atgaggattt tgcatgaaaa aaatccttt tataacaggc    4860 tctagggctg attattctaa gattaaatct ttaatgtaca gggtgcaaaa ctcaagcgaa    4920
tttgaacttt acatctttgc aacaggaatg cacttaagta aaaattttgg ctatacagtt    4980
aaagaacttt ataaaaatgg ctttaaaaat atttatgaat ttataaatta tgataaatat    5040
tatcaaactg ataaggcttt agctactaca attgatggat tttcaaggta tgcaaatgag    5100
ctaaaacctg atttaatcgt agtacatgga gatagaattg agcctttagc agcagctatt    5160
gttggagcat taaataatat cttagtagcg catattgaag gcggagagat ttcaggaact    5220
attgacgata gcttacgcca cgctatatca aaactagctc atattcattt agtaaatgat    5280
gagtttgcaa aaggcgtttt aatgcagctt ggagaagatg aaaaatctat ttttatcata    5340
ggttcgcctg atttagaact tttaaacgat aataaaattt cacttagcga agcaaaaaaa    5400
tattatgata taaattatga aaactacgct ttgcttatgt ttcatcctgt tacaactgaa    5460
attactagca ttaaaaatca agcagacaat ttagtaaaag cactgataca aagtaataaa    5520
aattatattg ttatttatcc aaataatgat ttaggttttg aattaatctt gcaaagctat    5580
gaagagttta aaaataaccc tagatttaag ctttttccat cgcttagatt tgagtatttt    5640
ataactttgt taaaaatgc tgattttata ataggtaatt caagttgtat tttaaaagag    5700
gccttatact taaaacagc agggatttta gttggctcaa gacaaaatgg aagacttggc    5760
aatgaaaata cactaaaagt taatgcaaat agtgatgaaa tactaaaagc tattaacact    5820
attcataaaa aacaagattt atttagcgct aagttagaga ttttagatag ctcaaaatta    5880
ttttttgaat atttcaaag cggagatttt tttaaactca gcacacaaaa agttttaag    5940 gatataaaat gagcttagca ataatccctg ctcgtggtgg ctcaaagggt attaaaaata    6000
aaaatttggt tttattaaac aataaaacctt taatttacta cacgatcaaa gctgcactaa    6060
atgctaaaag cattagtaaa gttgttgtaa gcagtgatag tgatgaaatt ttaaattatg    6120
caaaaagtca aaatgttgat attttaaaac gcccaattag ccttgcacaa gatgatacca    6180
caagcgataa agtgctgtta catgctctaa aattttataa agattatgaa gatgtagttt    6240
ttttacaacc cacttcaccg ctaagaacaa atattcatat taatgaagct tttaatcttt    6300
ataaaaatag caatgcaaat gccctaatta gcgtaagcga atgtgataat aaaattctaa    6360 aagccttttgt ttgtaatgat tgtggcgatt tagcagggat tgtaatgat gaatatcctt    6420 ttatgccaag gcaaaaattg cctaaaactt atatgagcaa tggtgcaatt tatattttaa    6480
agataaaaga atttttaaac aatcctagct ttttacaaag caaaaccaag cattttttaa    6540
tggacgaaag ctcaagttta gatattgact gtttggagga tttaaaaaag gttgaacaga    6600
tatggaaaaa ataactcgag caccaccacc accaccactg atccggctgc taagatagct    6660
tgacctgtga agtgaaaaat ggcgcacatt gtgcgacatt ttttttgtct gccgtttacc    6720
gctactgcgt cacggatccc cacgcgccct gtagcggcgc attaagcgcg gcgggtgtgg    6780
tggttacgcg cagcgtgacc gctacacttg ccagcgccct agcgcccgct cctttcgctt    6840
tcttcccttc ctttctcgcc acgttcgccg gctttccccg tcaagctcta aatcgggggc    6900
tccctttagg gttccgattt agtgctttac ggcacctcga ccccaaaaaa cttgattagg    6960
gtgatggttc acgtagtggg ccatcgccct gatagacggt tttcgccct ttgacgttgg    7020 agtccacgtt ctttaatagt ggactcttgt tccaaactgg aacaacactc aaccctatct    7080
```

```
cggtctattc tttttgattta taagggattt tgccgatttc ggcctattgg ttaaaaaatg    7140
agctgattta acaaaaattt aacgcgaatt ttaacaaaat attaacgctt acaatttcag    7200
gtggcacttt tcggggaaat gtgcgcggaa cccctatttg tttattttc taaatacatt    7260 caaatatgta tccgctcatg agacaataac cctgataaat gcttcaataa tattgaaaaa    7320
ggaagagtat gagtattcaa catttccgtg tcgcccttat tcccttttt gcggcatttt    7380 gccttcctgt ttttgctcac ccagaaacgc tggtgaaagt aaaagatgct gaagatcagt    7440
tgggtgcacg agtgggttac atcgaactgg atctcaacag cggtaagatc cttgagagtt    7500
ttcgccccga agaacgtttt ccaatgatga gcacttttaa agttctgcta tgtggcgcgg    7560
tattatcccg tattgacgcc gggcaagagc aactcggtcg ccgcatacac tattctcaga    7620
atgacttggt tgagtactca ccagtcacag aaaagcatct tacgatggc atgacagtaa    7680 gagaattatg cagtgctgcc ataaccatga gtgataacac tgcggccaac ttacttctga    7740
caacgatcgg aggaccgaag gagctaaccg cttttttgca caacatgggg gatcatgtaa    7800
ctcgccttga tcgttgggaa ccggagctga atgaagccat accaaacgac gagcgtgaca    7860
ccacgatgcc tgtagcaatg gcaacaacgt tgcgcaaact attaactggc gaactactta    7920
ctctagcttc ccggcaacaa ttaatagact ggatggaggc ggataaagtt gcaggaccac    7980
ttctgcgctc ggcccttccg gctggctggt ttattgctga taaatctgga gccggtgagc    8040
gtgggtctcg cggtatcatt gcagcactgg ggccagatgg taagccctcc cgtatcgtag    8100
ttatctacac gacggggagt caggcaacta tggatgaacg aaatagacag atcgctgaga    8160
taggtgcctc actgattaag cattggtaac tgtcagacca agtttactca tatatacttt    8220
agattgattt aaaacttcat ttttaattta aaaggatcta ggtgaagatc ctttttgata    8280
atctcatgac caaaatccct taacgtgagt tttcgttcca ctgagcgtca gaccccgtag    8340
aaaagatcaa aggatcttct tgagatcctt ttttctgcg cgtaatctgc tgcttgcaaa    8400
caaaaaaacc accgctacca gcggtggttt gtttgccgga tcaagagcta ccaactcttt    8460
ttccgaaggt aactggcttc agcagagcgc agataccaaa tactgttctt ctagtgtagc    8520
cgtagttagg ccaccacttc aagaactctg tagcaccgcc tacatacctc gctctgctaa    8580
tcctgttacc agtggctgct gccagtggcg ataagtcgtg tcttaccggg ttggactcaa    8640
gacgatagtt accggataag gcgcagcggt cgggctgaac ggggggttcg tgcacacagc    8700
ccagcttgga gcgaacgacc tacaccgaac tgagatacct acagcgtgag ctatgagaaa    8760
gcgccacgct tcccgaaggg agaaaggcgg acaggtatcc ggtaagcggc agggtcggaa    8820
caggagagcg cacgagggag cttccagggg gaaacgcctg gtatctttat agtcctgtcg    8880
ggtttcgcca cctctgactt gagcgtcgat ttttgtgatg ctcgtcaggg gggcggagcc    8940
tatggaaaaa cgccagcaac gcggcctttt tacggttcct ggccttttgc tggccttttg    9000
ctcacatg                                                             9008
```

<210> SEQ ID NO 6  
<211> LENGTH: 4125  
<212> TYPE: DNA  
<213> ORGANISM: Artificial Sequence  
<220> FEATURE:  
<223> OTHER INFORMATION: synthetic

<400> SEQUENCE: 6

```
acccgacacc atcgaatggc gcaaaacctt tcgcggtatg gcatgatagc gcccggaaga    60
gagtcaattc agggtggtga atgtgaaacc agtaacgtta tacgatgtcg cagagtatgc    120
```

```
cggtgtctct tatcagaccg tttcccgcgt ggtgaaccag gccagccacg tttctgcgaa    180
aacgcgggaa aaagtggaag cggcgatggc ggagctgaat tacattccca accgcgtggc    240
acaacaactg gcgggcaaac agtcgttgct gattggcgtt gccacctcca gtctggccct    300
gcacgcgccg tcgcaaattg tcgcggcgat taaatctcgc gccgatcaac tgggtgccag    360
cgtggtggtg tcgatggtag aacgaagcgg cgtcgaagcc tgtaaagcgg cggtgcacaa    420
tcttctcgcg caacgcgtca gtgggctgat cattaactat ccgctggatg accaggatgc    480
cattgctgtg gaagctgcct gcactaatgt tccggcgtta tttcttgatg tctctgacca    540
gacacccatc aacagtatta ttttctccca tgaagacggt acgcgactgg gcgtggagca    600
tctggtcgca ttgggtcacc agcaaatcgc gctgttagcg ggcccattaa gttctgtctc    660
ggcgcgtctg cgtctggctg gctggcataa atatctcact cgcaatcaaa ttcagccgat    720
agcggaacgg gaaggcgact ggagtgccat gtccggtttt caacaaacca tgcaaatgct    780 gaatgaggc atcgttccca ctgcgatgct ggttgccaac gatcagatgg cgctgggcgc    840
aatgcgcgcc attaccgagt ccgggctgcg cgttggtgcg gacatctcgg tagtgggata    900
cgacgatacc gaagacagct catgttatat cccgccgtta accaccatca acaggatt    960 tcgcctgctg gggcaaacca gcgtggaccg cttgctgcaa ctctctcagg gccaggcggt    1020
gaagggcaat cagctgttgc ccgtctcact ggtgaaaaga aaaccacccc tggcgcccaa    1080
tacgcaaacc gcctctcccc gcgcgttggc cgattcatta atgcagctgg cacgacaggt    1140
ttcccgactg gaaagcgggc agtgagcgca acgcaattaa tgtgagttag ctcactcatt    1200
aggcacccca ggctttacac tttatgcttc cggctcgtat gttgtgtgga attgtgagcg    1260
gataacaatt tcacacagga aacagctatg accatgatta cgaatttcta gataacgagg    1320
gcaaaaaatg aaaaagacag ctatcgcgat tgcagtggca ctggctggtt tcgctaccgt    1380
agcgcaggcc gactacaaag atatccgtga cctggaagtg gtcgctgcca caccgacgag    1440
tctgctgatt tcttgggatg caccagctgt aaccgtgcgc tactaccgca ttacttacgg    1500
ggagacgggc ggcaattccc cggtgcaaga atttactgtt ccgggcagca aaagtacagc    1560
aactattagc ggcctgaaac cgggcgttga ttataccatt actgtttacg cagtaactgg    1620
gcgtggcgat tcaccggcgt cctctaaacc tatttcgatc aactatcgta ctgaaatcgg    1680
tggtggtggt tctgaccaaa acgcgaccaa gcttggtggt ggtggttcac tcgagcacca    1740
ccaccaccac cactgagatc cggctgctaa gatagcttga cctgtgaagt gaaaaatggc    1800
gcacattgtg cgacattttt tttgtctgcc gtttaccgct actgcgtcac ggatccccac    1860
gcgccctgta gcggcgcatt aagcgcggcg ggtgtggtgg ttacgcgcag cgtgaccgct    1920
acacttgcca gcgccctagc gcccgctcct ttcgctttct tcccttcctt tctcgccacg    1980
ttcgccggct ttccccgtca agctctaaat cgggggctcc ctttagggtt ccgatttagt    2040
gctttacggc acctcgaccc caaaaaactt gattagggtg atggttcacg tagtgggcca    2100
tcgccctgat agacggtttt tcgccctttg acgttggagt ccacgttctt taatagtgga    2160
ctcttgttcc aaactggaac aacactcaac cctatctcgg tctattcttt tgatttataa    2220
gggattttgc cgatttcggc ctattggtta aaaaatgagc tgatttaaca aaaatttaac    2280
gcgaatttta caaaatatt aacgcttaca atttcaggtg gcacttttcg gggaaatgtg    2340
cgcggaaccc ctatttgttt attttttctaa atacattcaa atatgtatcc gctcatgaga    2400
caataaccct gataaatgct tcaataatat tgaaaaagga agagtatgag tattcaacat    2460
```

```
ttccgtgtcg cccttattcc cttttttgcg gcattttgcc ttcctgtttt tgctcaccca   2520
gaaacgctgg tgaaagtaaa agatgctgaa gatcagttgg gtgcacgagt gggttacatc   2580
gaactggatc tcaacagcgg taagatcctt gagagttttc gccccgaaga acgttttcca   2640
atgatgagca cttttaaagt tctgctatgt ggcgcggtat tatcccgtat tgacgccggg   2700
caagagcaac tcggtcgccg catacactat tctcagaatg acttggttga gtactcacca   2760
gtcacagaaa agcatcttac ggatggcatg acagtaagag aattatgcag tgctgccata   2820
accatgagtg ataacactgc ggccaactta cttctgacaa cgatcggagg accgaaggag   2880
ctaaccgctt ttttgcacaa catgggggat catgtaactc gccttgatcg ttgggaaccg   2940
gagctgaatg aagccatacc aaacgacgag cgtgacacca cgatgcctgt agcaatggca   3000
acaacgttgc gcaaactatt aactggcgaa ctacttactc tagcttcccg gcaacaatta   3060
atagactgga tggaggcgga taaagttgca ggaccacttc tgcgctcggc ccttccggct   3120
ggctggttta ttgctgataa atctggagcc ggtgagcgtg ggtctcgcgg tatcattgca   3180
gcactggggc cagatggtaa gccctcccgt atcgtagtta tctacacgac ggggagtcag   3240
gcaactatgg atgaacgaaa tagacagatc gctgagatag gtgcctcact gattaagcat   3300
tggtaactgt cagaccaagt ttactcatat atactttaga ttgatttaaa acttcatttt   3360
taatttaaaa ggatctaggt gaagatcctt tttgataatc tcatgaccaa aatcccttaa   3420
cgtgagtttt cgttccactg agcgtcagac cccgtagaaa agatcaaagg atcttcttga   3480
gatccttttt ttctgcgcgt aatctgctgc ttgcaaacaa aaaaaccacc gctaccagcg   3540
gtggtttgtt tgccggatca agagctacca actctttttc cgaaggtaac tggcttcagc   3600
agagcgcaga taccaaatac tgttcttcta gtgtagccgt agttaggcca ccacttcaag   3660
aactctgtag caccgcctac atacctcgct ctgctaatcc tgttaccagt ggctgctgcc   3720
agtggcgata agtcgtgtct taccgggttg gactcaagac gatagttacc ggataaggcg   3780
cagcggtcgg gctgaacggg gggttcgtgc acacagccca gcttggagcg aacgacctac   3840
accgaactga gatacctaca gcgtgagcta tgagaaagcg ccacgcttcc cgaagggaga   3900
aaggcggaca ggtatccggt aagcggcagg gtcggaacag gagagcgcac gagggagctt   3960
ccaggggaa acgcctggta tctttatagt cctgtcgggt ttcgccacct ctgacttgag   4020
cgtcgatttt tgtgatgctc gtcaggggg cggagcctat ggaaaaacgc cagcaacgcg   4080
gcctttttac ggttcctggc cttttgctgg ccttttgctc acatg   4125

<210> SEQ ID NO 7
<211> LENGTH: 57
<212> TYPE: DNA
<213> ORGANISM: Artificial Sequence
<220> FEATURE:
<223> OTHER INFORMATION: synthetic

<400> SEQUENCE: 7
gcatccgcgc cagccaactc ccctgcgct gccgctgcgt gtaggctgga gctgctt    57

<210> SEQ ID NO 8
<211> LENGTH: 57
<212> TYPE: DNA
<213> ORGANISM: Artificial Sequence
<220> FEATURE:
<223> OTHER INFORMATION: synthetic

<400> SEQUENCE: 8
tggtgtacaa cattccagcc ctgagtgggg taaaactctg tcaaacatga gaattaa    57
```

<210> SEQ ID NO 9
<211> LENGTH: 59
<212> TYPE: DNA
<213> ORGANISM: Artificial Sequence
<220> FEATURE:
<223> OTHER INFORMATION: synthetic

<400> SEQUENCE: 9
gtcaccctgc ccggcgcgcg tgaaaatagt tttcgcatcc gcgccagcca actccccct    59

<210> SEQ ID NO 10
<211> LENGTH: 59
<212> TYPE: DNA
<213> ORGANISM: Artificial Sequence
<220> FEATURE:
<223> OTHER INFORMATION: synthetic

<400> SEQUENCE: 10
gcaattattg attcggcgga tggtttgccg atggtggtgt acaacattcc agccctgag    59

<210> SEQ ID NO 11
<211> LENGTH: 12
<212> TYPE: PRT
<213> ORGANISM: Artificial Sequence
<220> FEATURE:
<223> OTHER INFORMATION: synthetic

<400> SEQUENCE: 11

Ile Gly Gly Gly Gly Ser Asp Gln Asn Ala Thr Lys
1               5                   10

<210> SEQ ID NO 12
<211> LENGTH: 4
<212> TYPE: PRT
<213> ORGANISM: Artificial Sequence
<220> FEATURE:
<223> OTHER INFORMATION: synthetic

<400> SEQUENCE: 12

Asp Tyr Lys Asp
1

<210> SEQ ID NO 13
<211> LENGTH: 5
<212> TYPE: PRT
<213> ORGANISM: Artificial Sequence
<220> FEATURE:
<223> OTHER INFORMATION: synthetic

<400> SEQUENCE: 13

Asp Gln Asn Ala Thr
1               5

<210> SEQ ID NO 14
<211> LENGTH: 20
<212> TYPE: DNA
<213> ORGANISM: Artificial Sequence
<220> FEATURE:
<223> OTHER INFORMATION: synthetic

<400> SEQUENCE: 14
cgcactggca atcagttgtg                                               20

<210> SEQ ID NO 15
<211> LENGTH: 20

```
<212> TYPE: DNA
<213> ORGANISM: Artificial Sequence
<220> FEATURE:
<223> OTHER INFORMATION: synthetic

<400> SEQUENCE: 15
cgtcacgccg ttctactatc                                           20
```